(12) United States Patent
Oura et al.

(10) Patent No.: US 11,737,735 B2
(45) Date of Patent: Aug. 29, 2023

(54) PATIENT MONITOR AND PHYSIOLOGICAL INFORMATION SYSTEM

(71) Applicant: NIHON KOHDEN CORPORATION, Tokyo (JP)

(72) Inventors: Mitsuhiro Oura, Tokyo (JP); Sou Kumagai, Tokyo (JP); Wataru Matsuzawa, Tokyo (JP); Nobuyuki Yasumaru, Tokyo (JP); Kazuya Nagase, Tokyo (JP); Hiroshi Torigai, Tokyo (JP); Naoki Fukushima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 324 days.

(21) Appl. No.: 16/766,162

(22) PCT Filed: Nov. 13, 2018

(86) PCT No.: PCT/JP2018/041937
§ 371 (c)(1),
(2) Date: May 21, 2020

(87) PCT Pub. No.: WO2019/102899
PCT Pub. Date: May 31, 2019

(65) Prior Publication Data
US 2020/0359999 A1 Nov. 19, 2020

(30) Foreign Application Priority Data
Nov. 22, 2017 (JP) .................................. 2017-224419

(51) Int. Cl.
*A61B 8/00* (2006.01)
*G06T 7/00* (2017.01)

(52) U.S. Cl.
CPC ................ *A61B 8/54* (2013.01); *A61B 8/463* (2013.01); *A61B 8/469* (2013.01); *G06T 7/0012* (2013.01);
(Continued)

(58) Field of Classification Search
CPC ........ A61H 31/005; A61B 8/02; A61B 8/065; A61B 8/0883; A61B 8/463; A61B 8/543;
(Continued)

(56) References Cited

U.S. PATENT DOCUMENTS

2003/0163045 A1* 8/2003 Gatzke ..................... A61B 8/12
600/437
2006/0058660 A1 3/2006 Sandy et al.
(Continued)

FOREIGN PATENT DOCUMENTS

CN  1879564 A  12/2006
JP  2006061469 A *  3/2006  ......... A61B 1/00045
(Continued)

OTHER PUBLICATIONS

Definition of "selected" (www.dictionary.com/browse/selected, retrieved Jan. 13, 2023).*
(Continued)

*Primary Examiner* — Carolyn A Pehlke
(74) *Attorney, Agent, or Firm* — Pearne & Gordon, LLP

(57) ABSTRACT

A physiological information system includes a patient monitor configured to acquire a vital sign based on a vital sign signal of a subject, and an ultrasonic measuring apparatus configured to acquire ultrasonic images based on ultrasonic waves transmitted toward the subject and received from the subject. The patient monitor includes a storage device configured to store measured data of the vital signs in association with measurement dates and times, and to store the ultrasonic images in association with image capture timings,
(Continued)

and a controller configured to display a screen on a display section based on data, including the measured data and the ultrasonic images, stored in the storage device.

19 Claims, 18 Drawing Sheets

(52) U.S. Cl.
CPC ............... *G06T 2200/24* (2013.01); *G06T 2207/10132* (2013.01); *G06T 2207/30004* (2013.01)

(58) Field of Classification Search
CPC ....... A61B 5/4821; A61B 5/352; A61B 5/353; A61B 5/355; A61B 5/357; A61B 5/358; A61B 5/346; A61B 5/36; A61B 5/361; A61B 5/363; A61B 5/364; A61B 5/366; A61B 5/024; A61B 5/0245; G16H 30/00; G16H 30/20; G16H 30/40; G16H 15/00; G16H 10/00; G16H 10/60; H04N 2201/3225; H04N 2201/3226; H04N 2201/3229
See application file for complete search history.

(56) References Cited

U.S. PATENT DOCUMENTS

| | | | |
|---|---|---|---|
| 2007/0016029 A1* | 1/2007 | Donaldson | A61B 8/565 600/437 |
| 2008/0009723 A1 | 1/2008 | Schefelker et al. | |
| 2008/0304730 A1* | 12/2008 | Abe | G06T 7/12 382/131 |
| 2009/0199128 A1* | 8/2009 | Matthews | G06F 3/04883 715/800 |
| 2013/0345563 A1* | 12/2013 | Stuebe | A61B 8/5223 600/440 |
| 2018/0296188 A1 | 10/2018 | Oura et al. | |

FOREIGN PATENT DOCUMENTS

| | | |
|---|---|---|
| JP | 2008-167838 A | 7/2008 |
| JP | 2012-135428 A | 7/2012 |
| JP | 2017-051594 A | 3/2017 |
| JP | 2017-086664 A | 5/2017 |
| WO | 2007-022505 A2 | 2/2007 |
| WO | 2009-138902 A1 | 11/2009 |
| WO | 2017-125991 A1 | 7/2017 |

OTHER PUBLICATIONS

Definition of "included" (www.dictionary.com/browse/included, retrieved Jan. 13, 2023).*
International Search Report Issued in Patent Application No. PCT/JP2018/041937 dated Feb. 22, 2019.
Written Opinion Issued in Patent Application No. PCT/JP2018/041937 dated Feb. 22, 2019.
Japanese Office Action dated Oct. 5, 2021 issued in Japanese Patent Application No. 2017-224419.

* cited by examiner

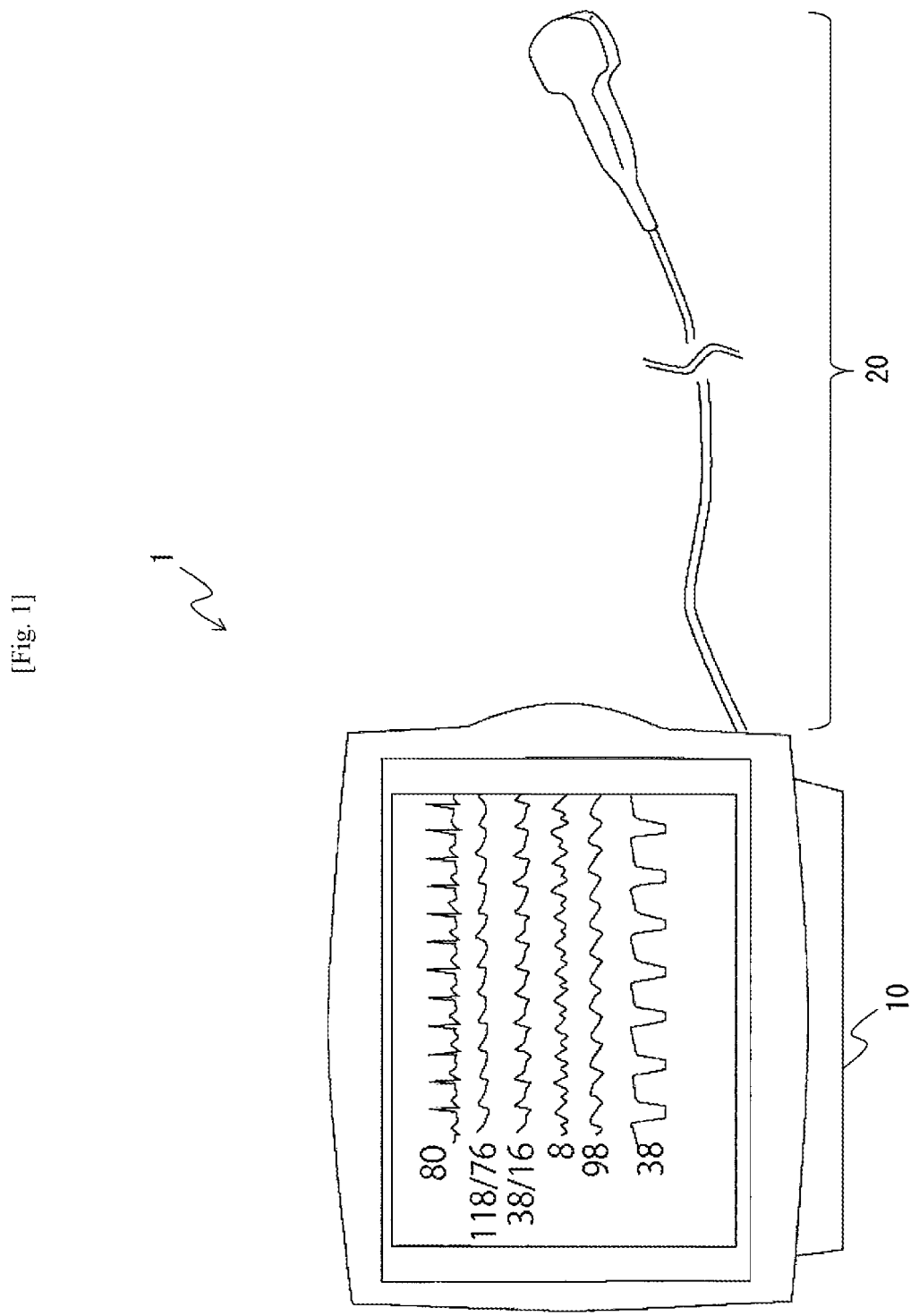

[Fig. 2]
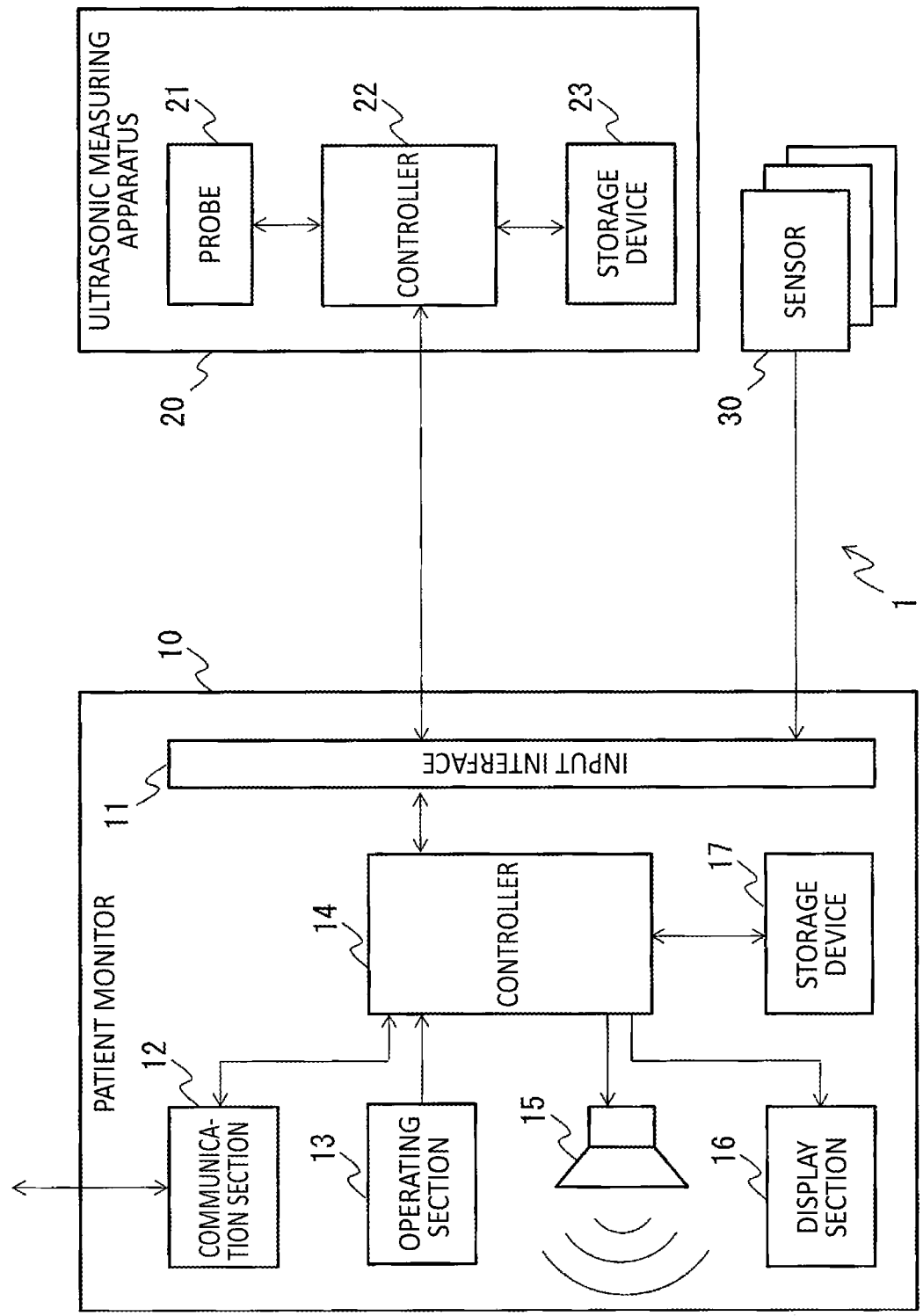

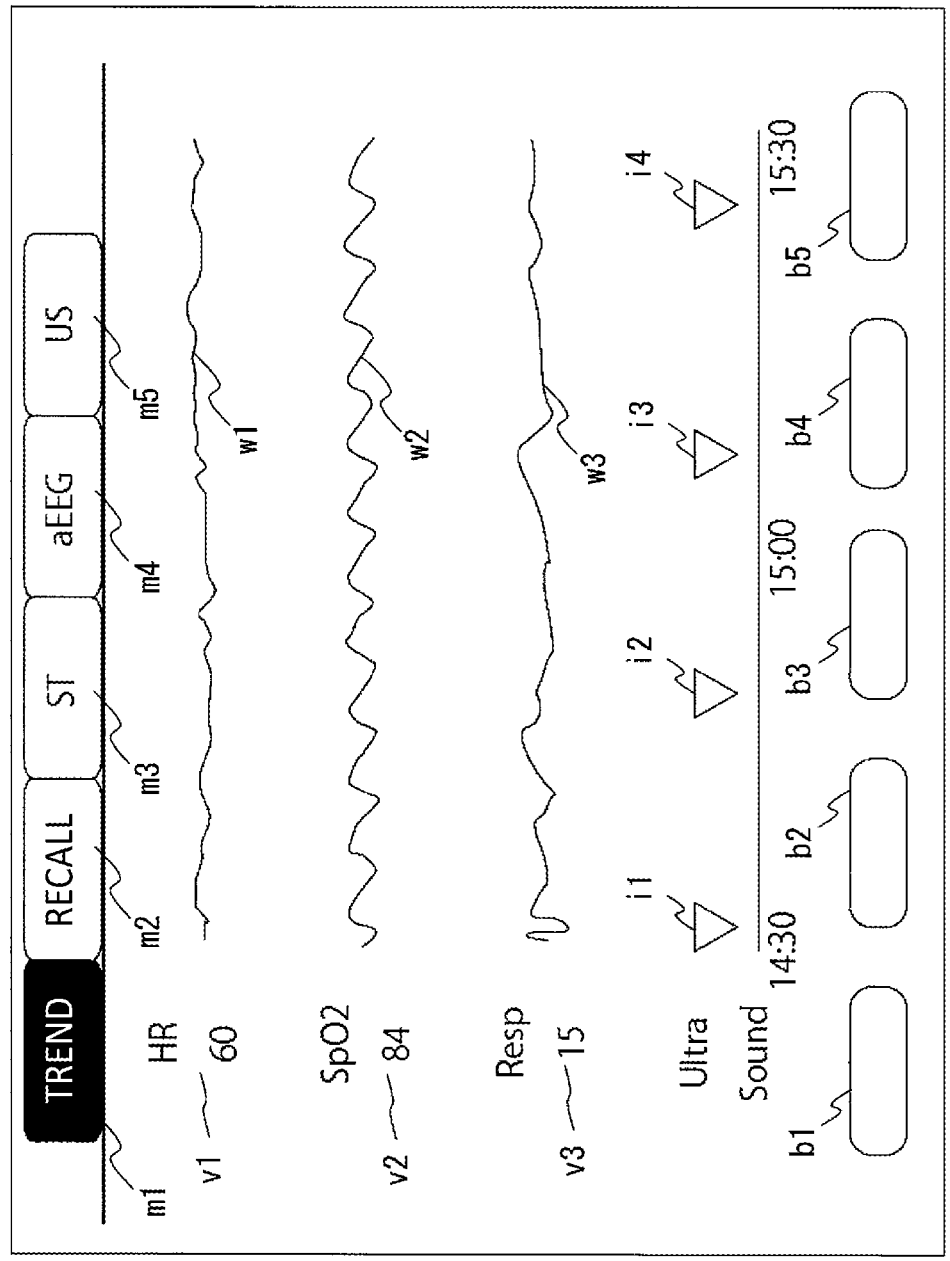
[Fig. 3]

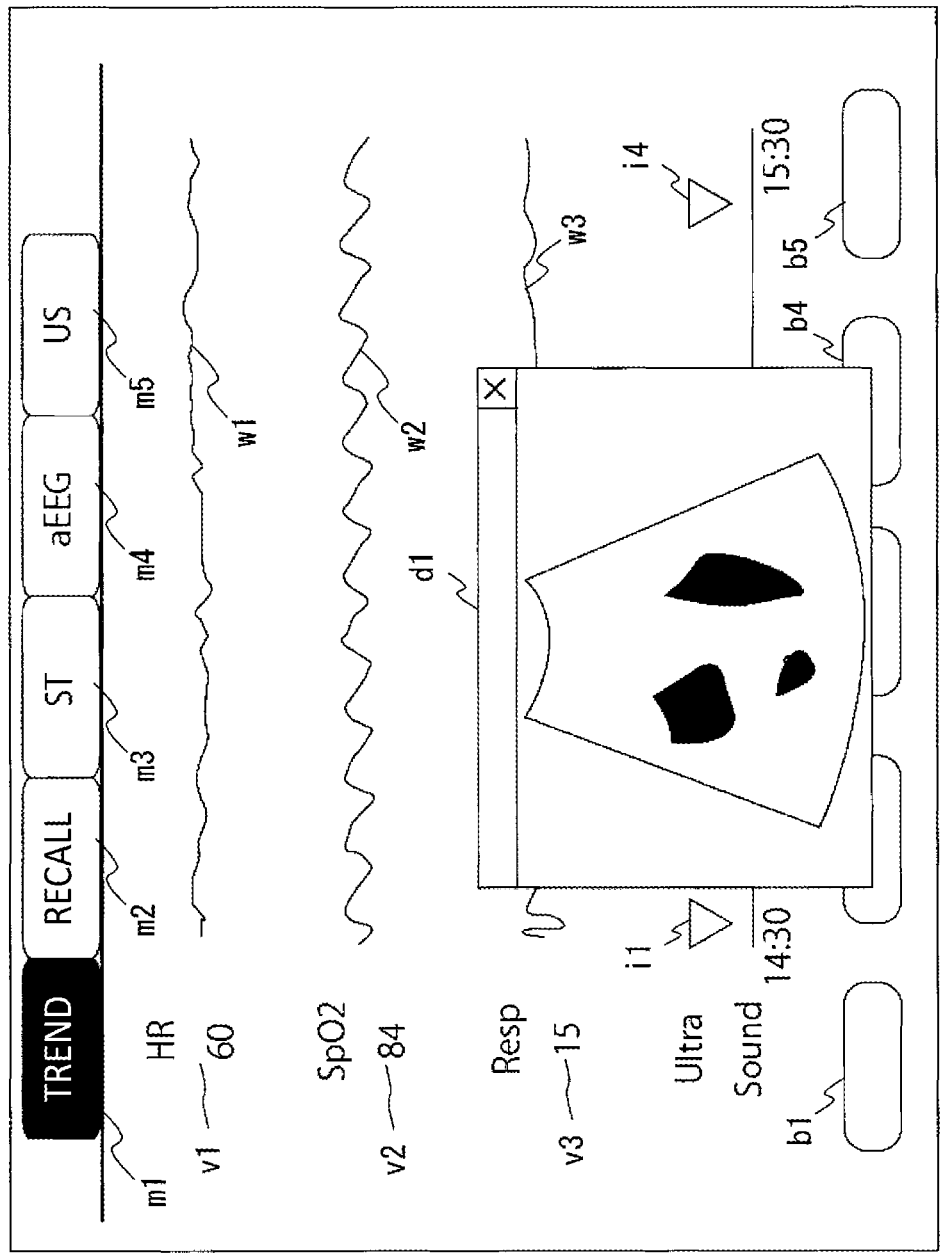
[Fig. 4]

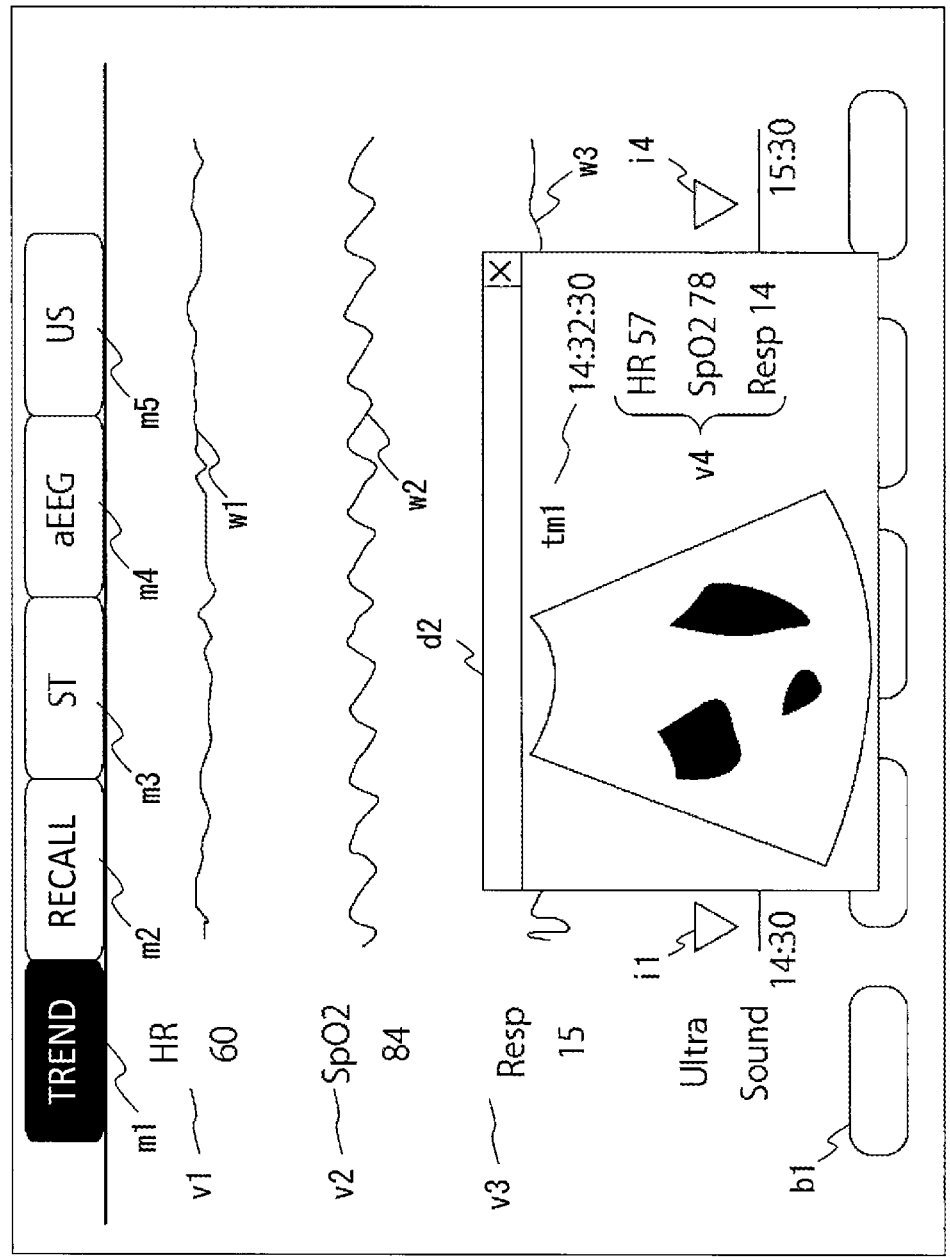
[Fig. 5]

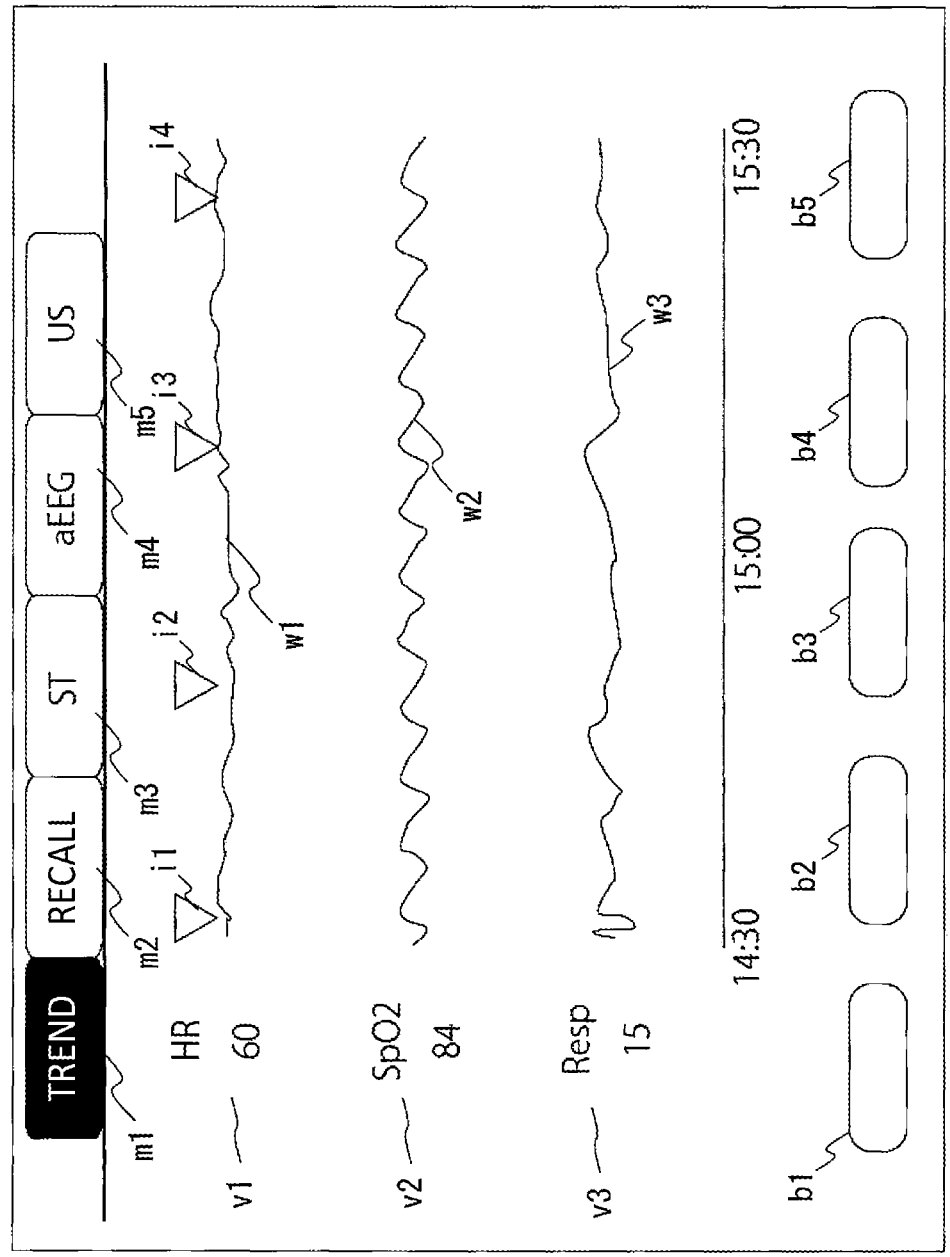
[Fig. 6]

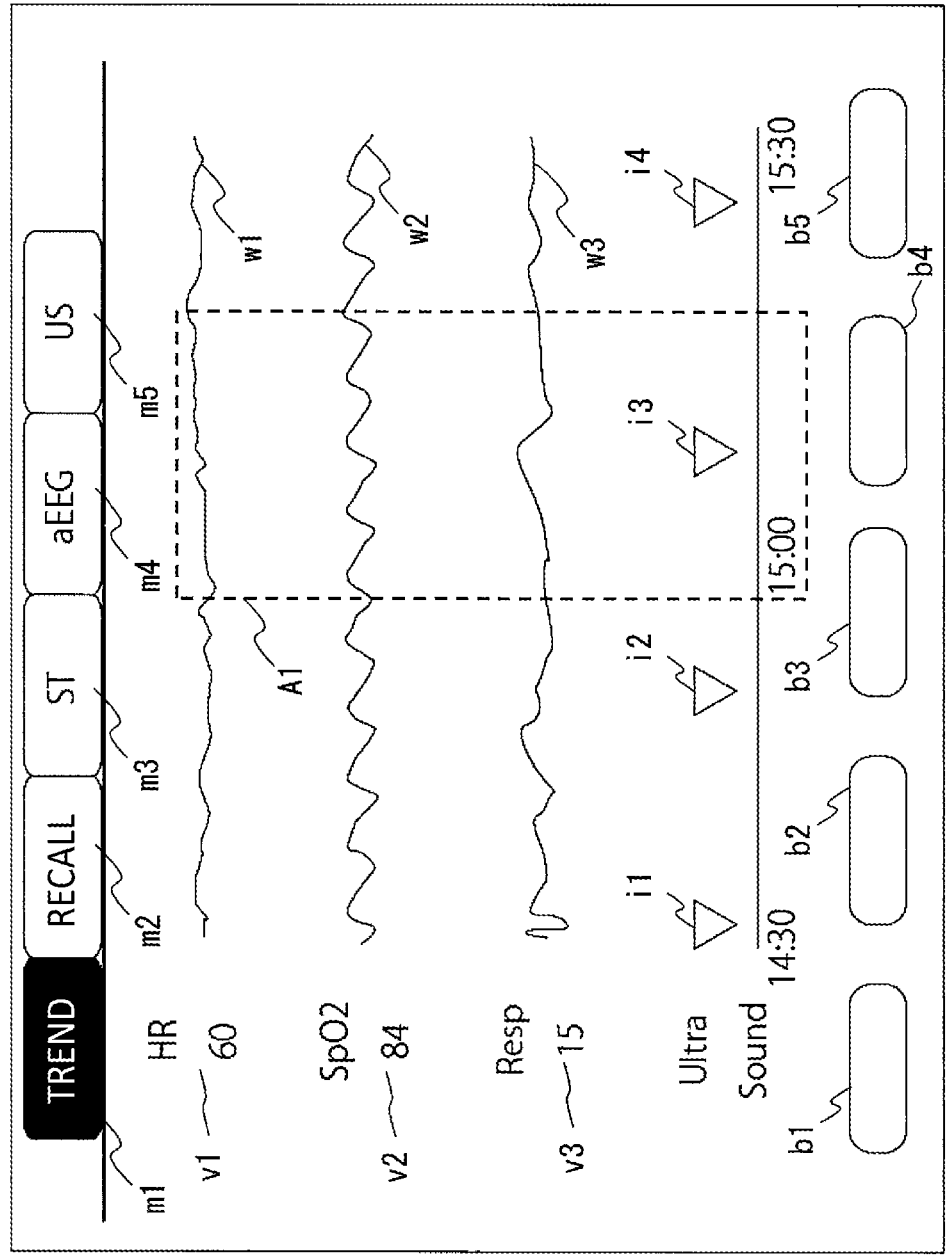
[Fig. 7]

[Fig. 8]
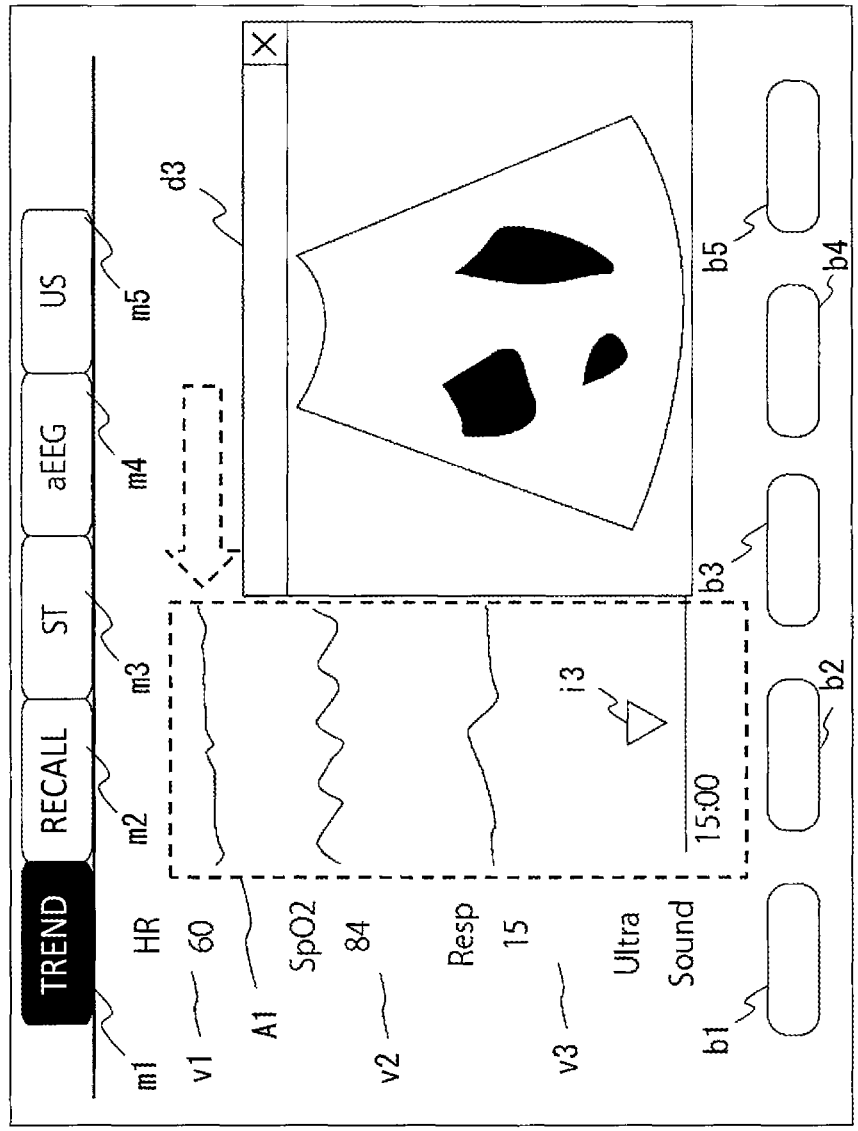

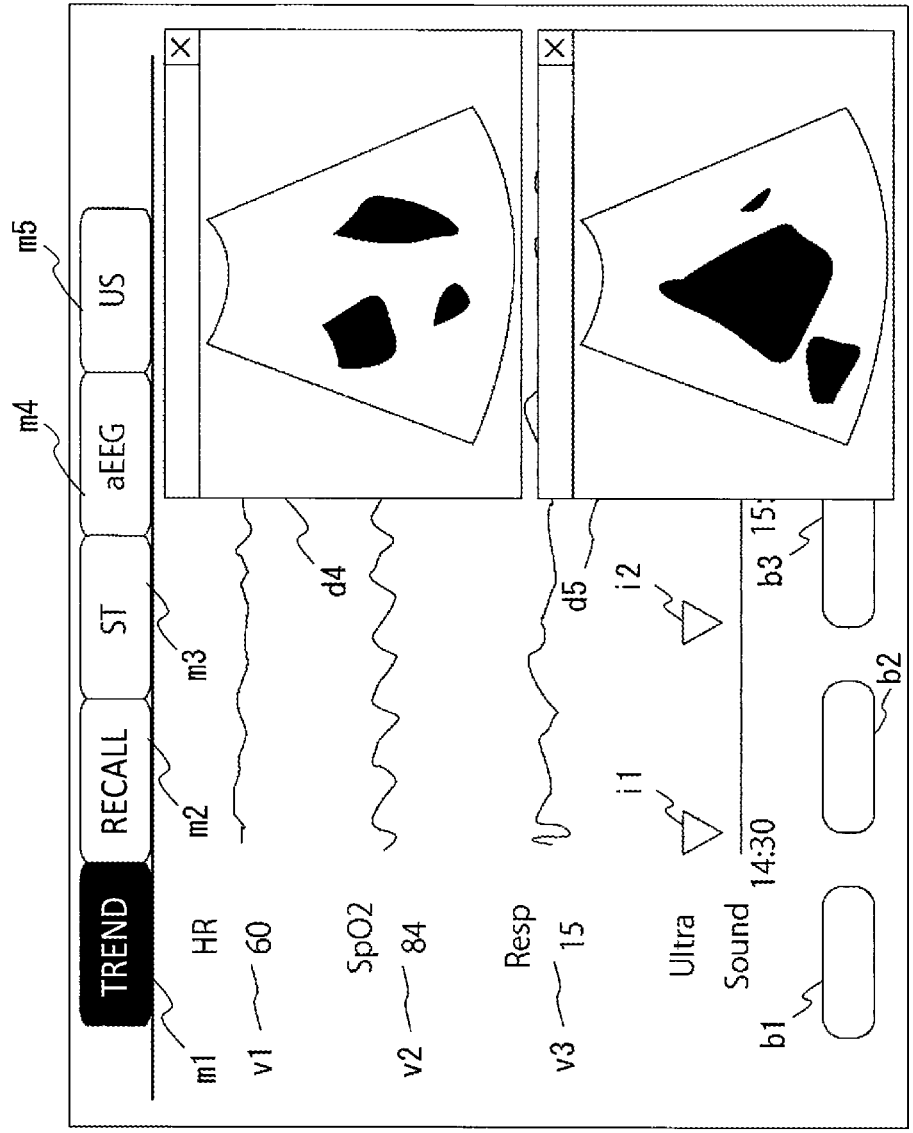

[Fig. 10]
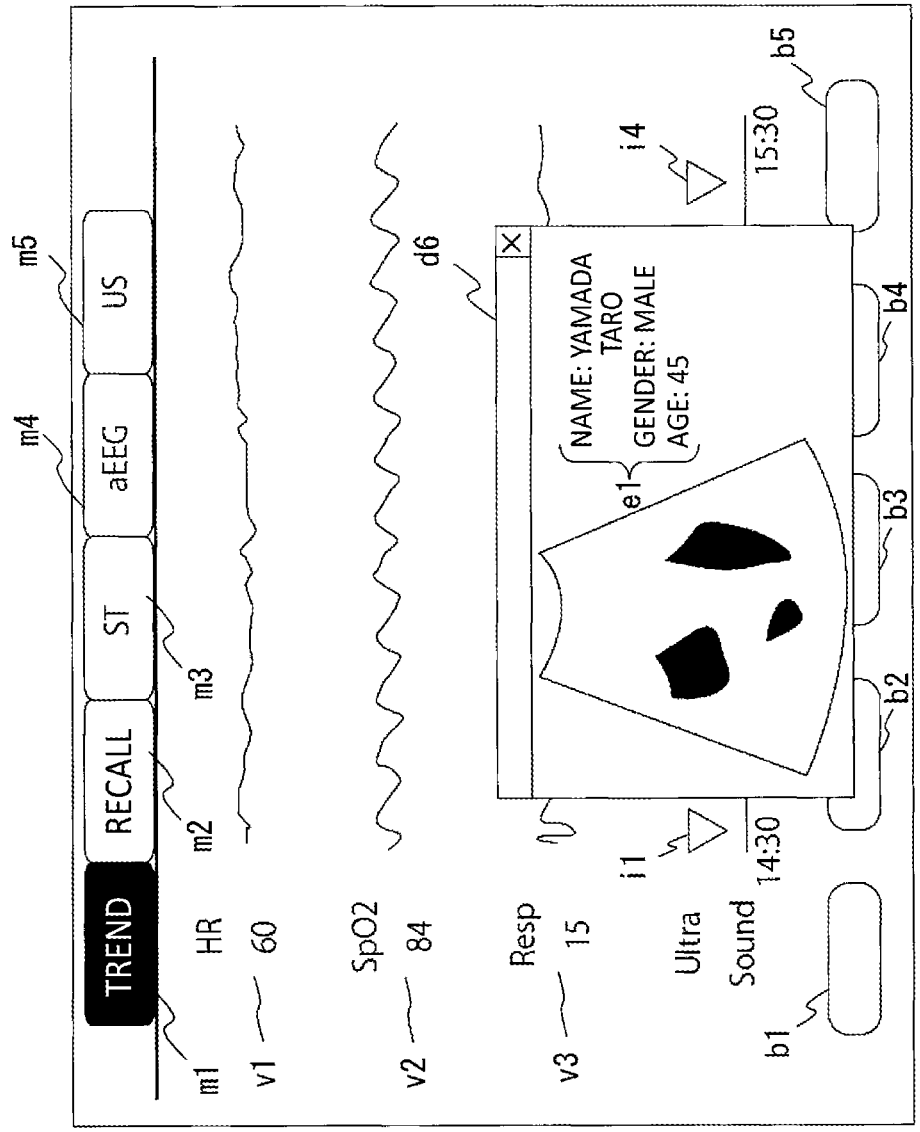

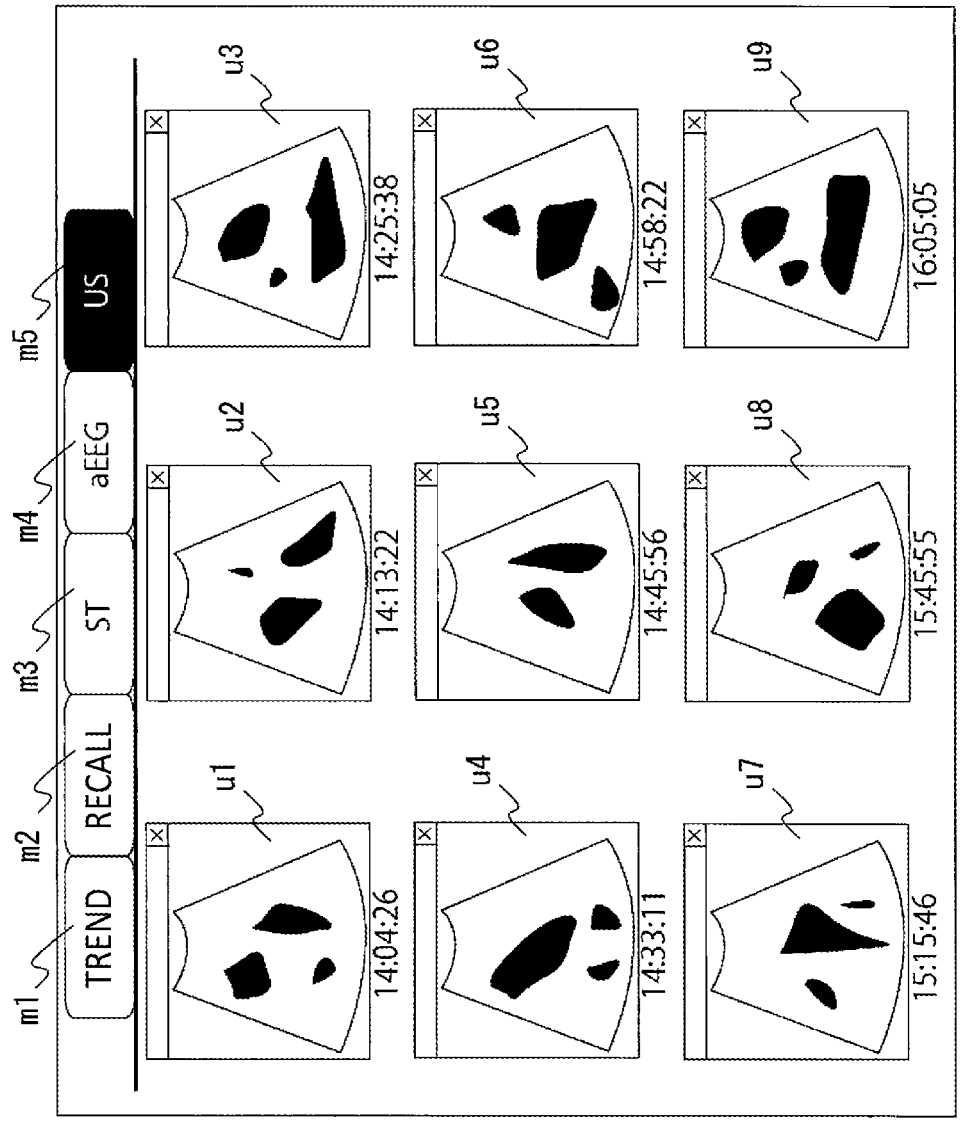
[Fig. 11]

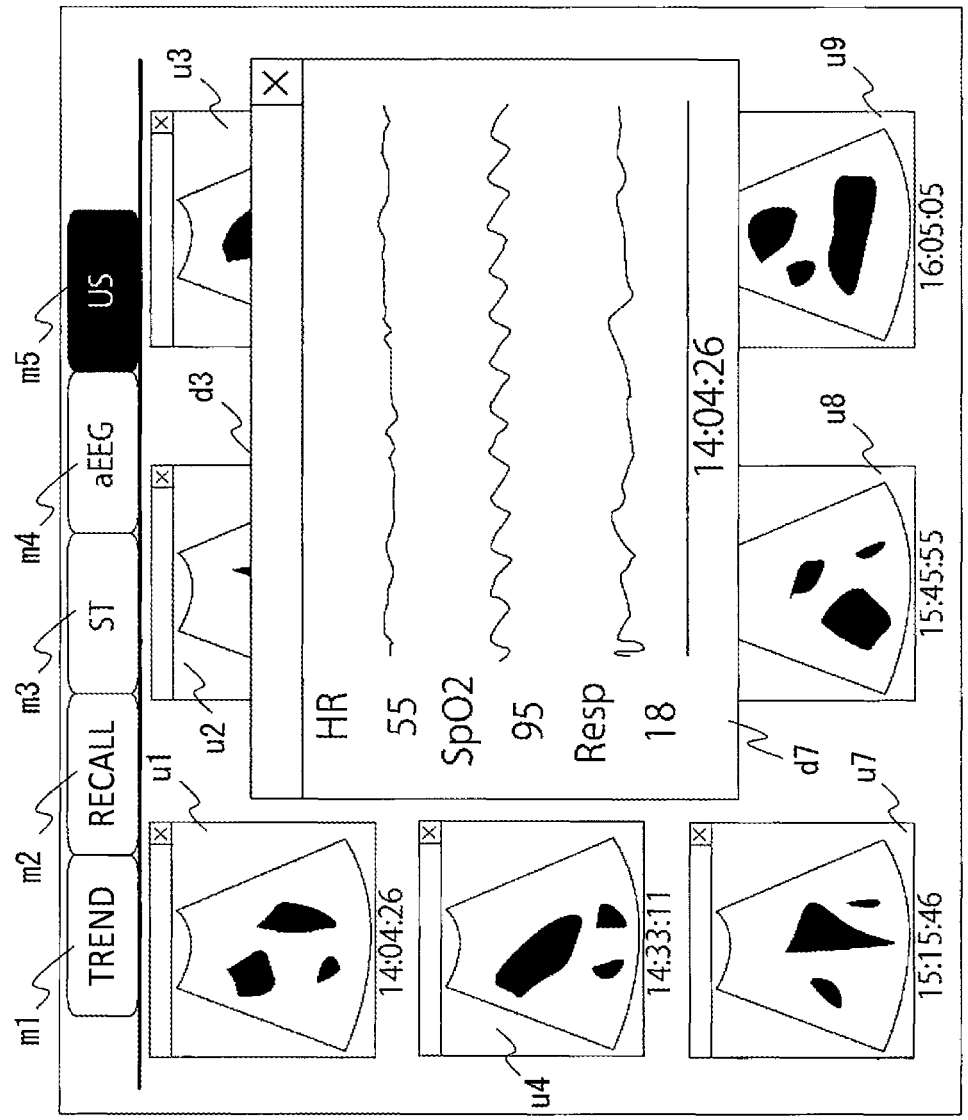
[Fig. 12]

[Fig. 13]
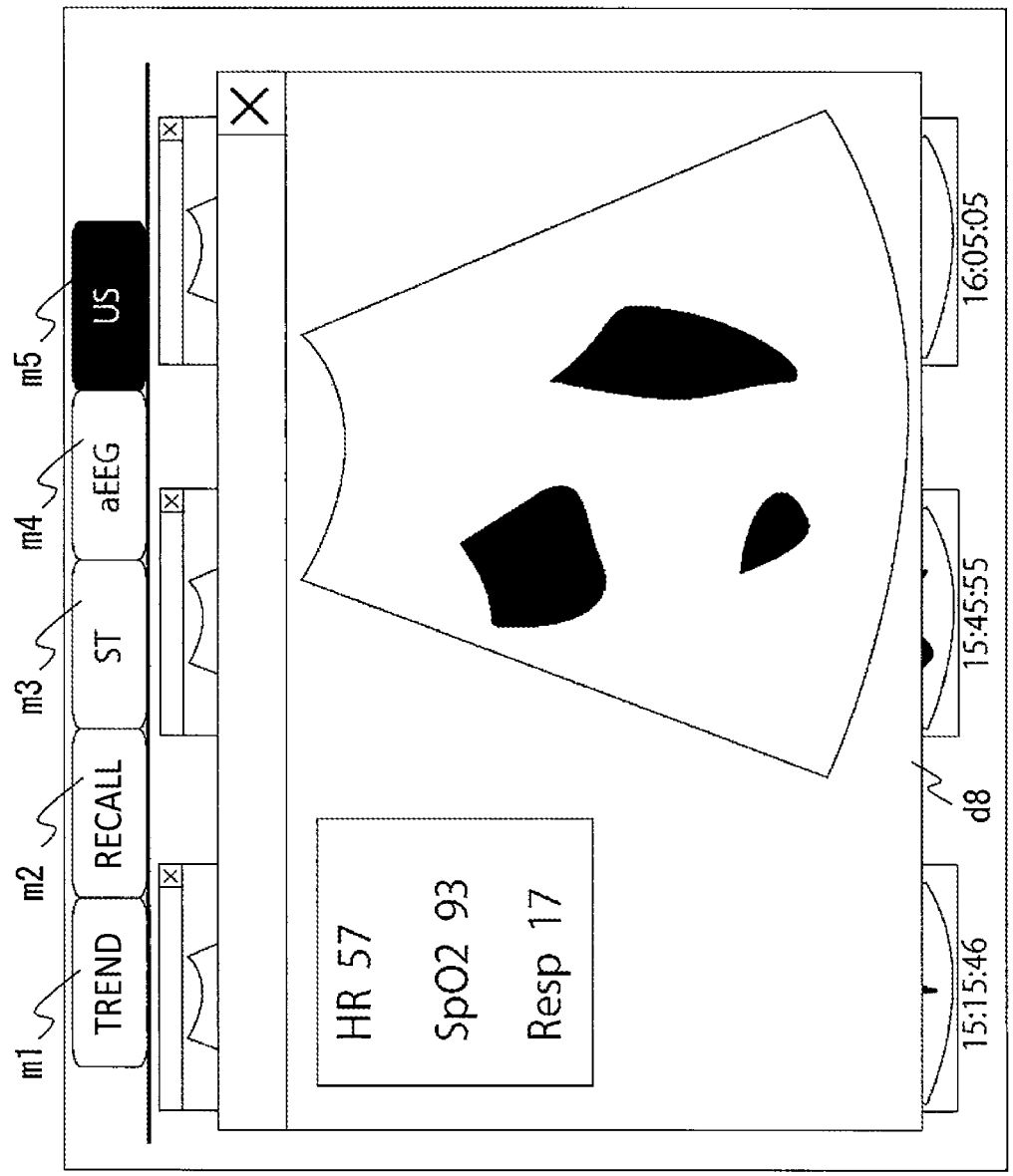

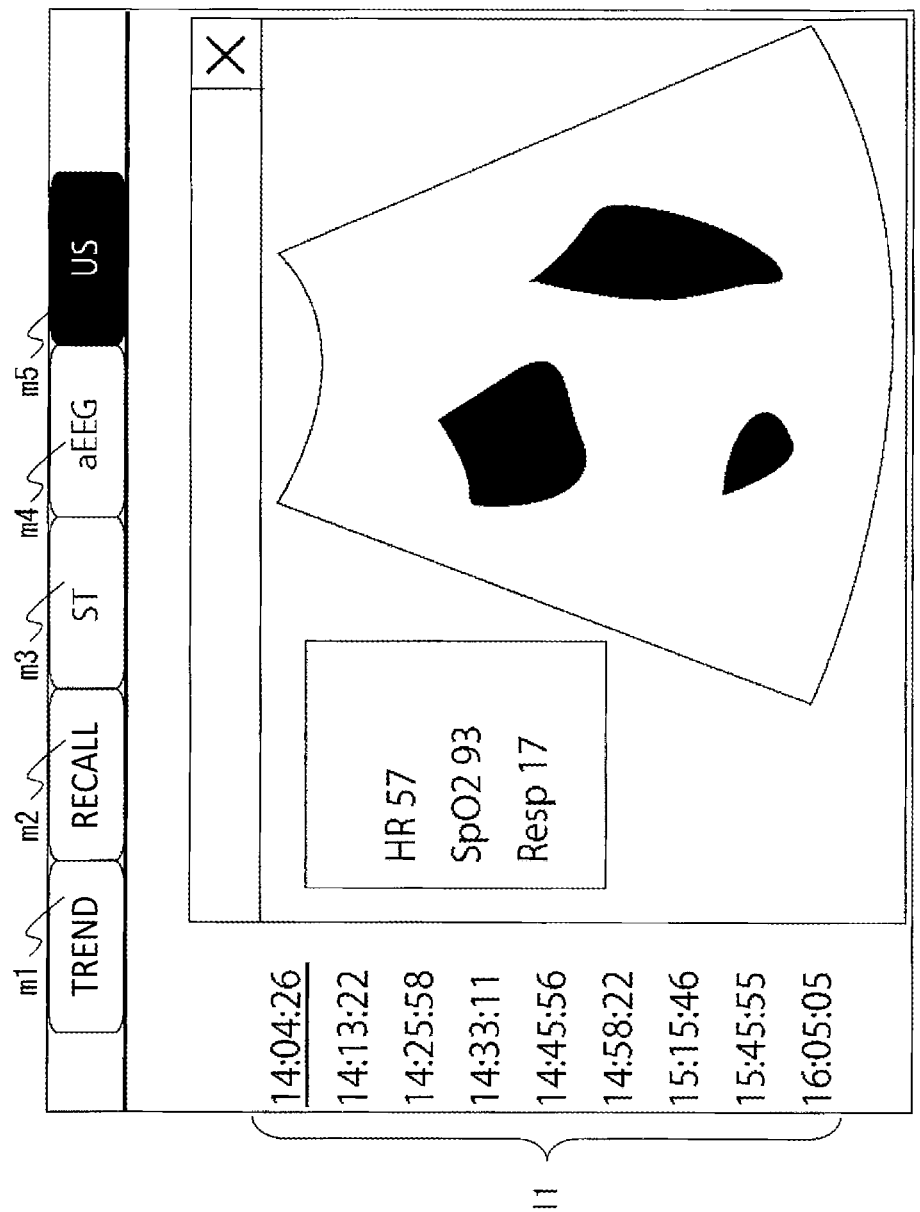
[Fig. 14]

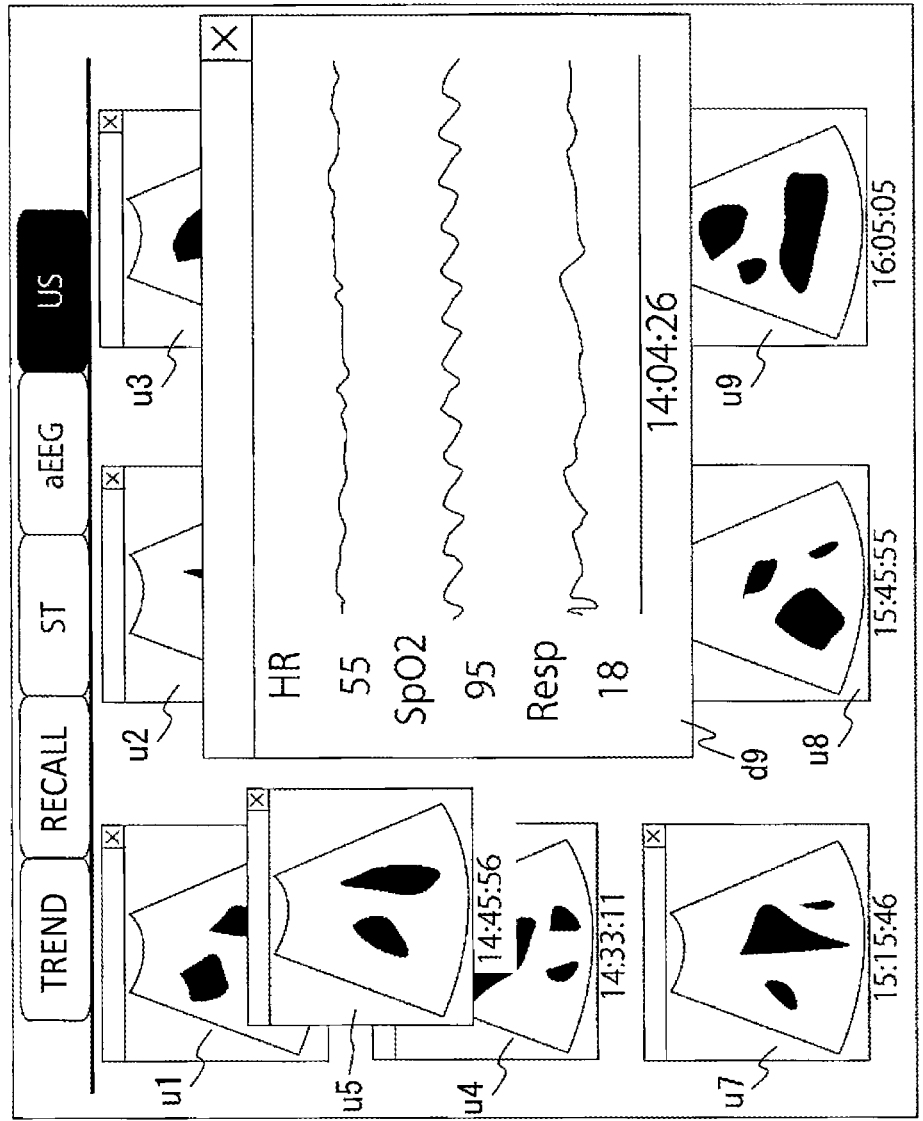
[Fig. 15]

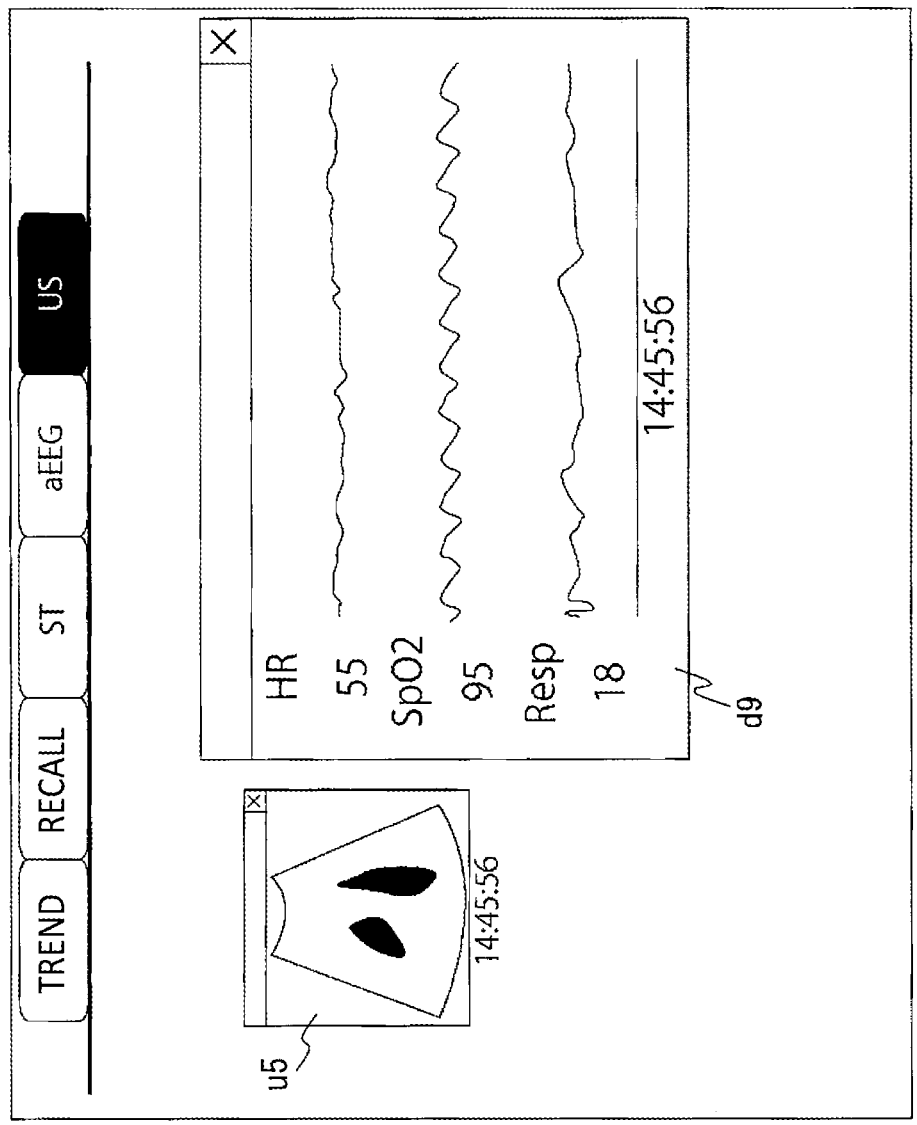

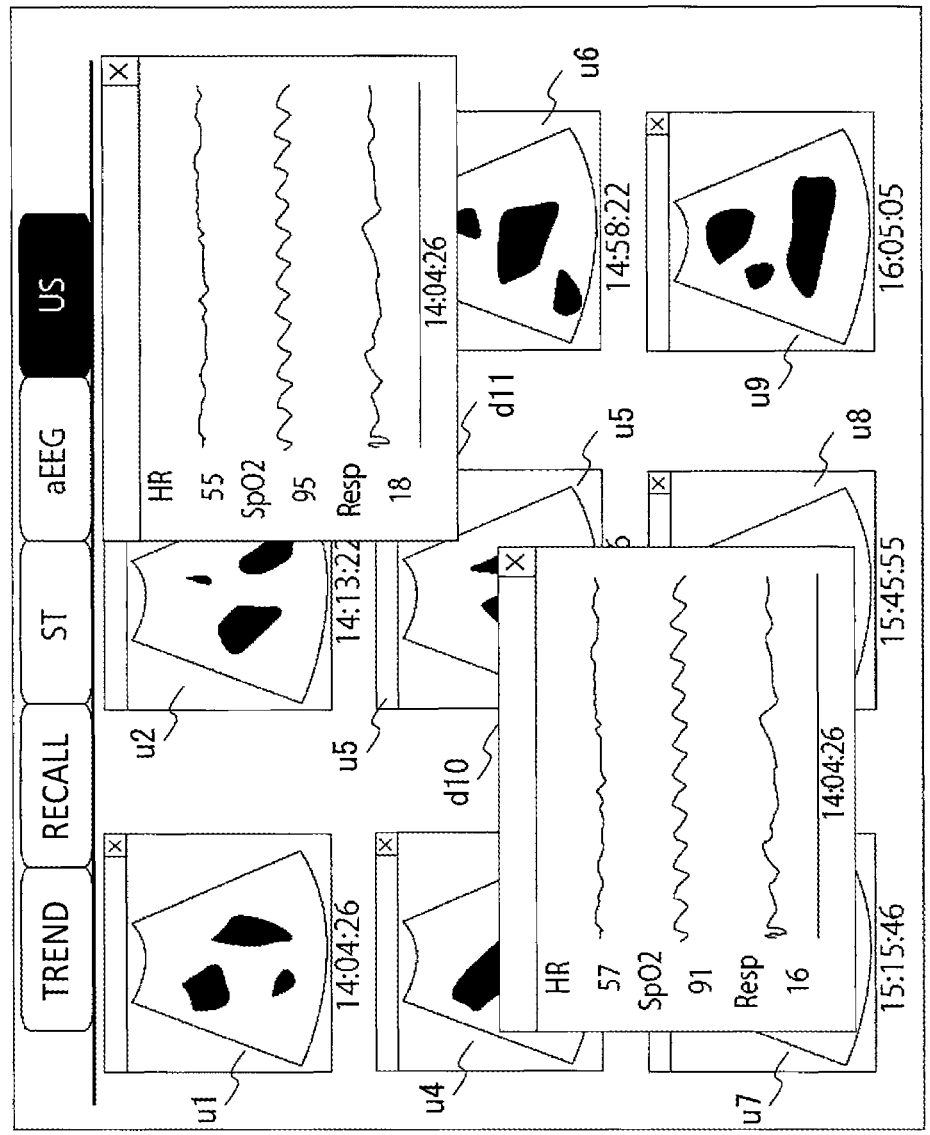

[Fig. 18]
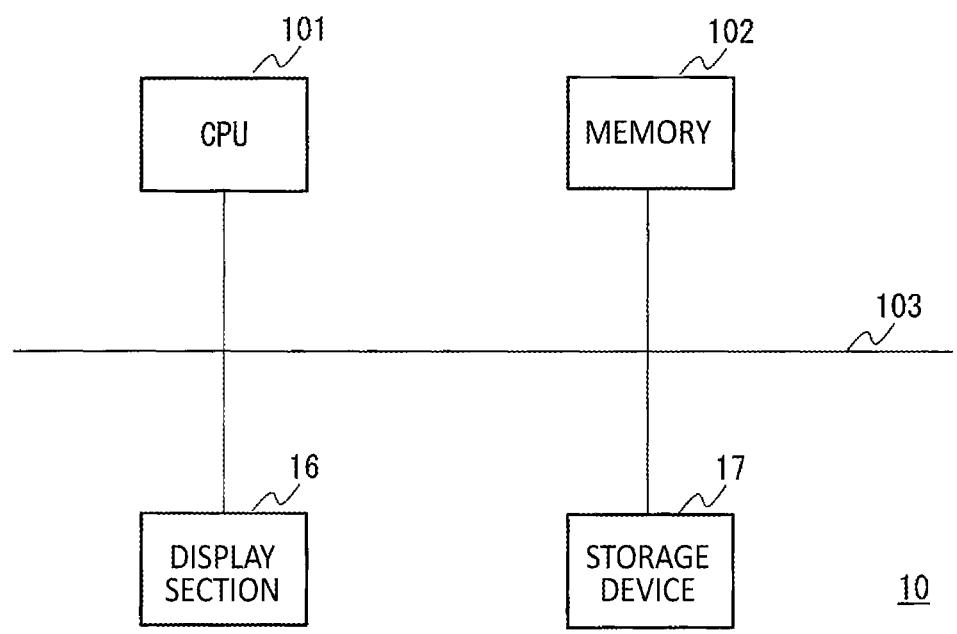

PATIENT MONITOR AND PHYSIOLOGICAL INFORMATION SYSTEM

TECHNICAL FIELD

The presently disclosed subject matter relates to a patient monitor and a physiological information system, in particular, to a patient monitor and a physiological information system acquiring ultrasonic images.

BACKGROUND ART

Various vital signs (blood pressure, body temperature, respiration, a pulse count, arterial oxygen saturation, etc.) have been widely used as information for grasping a condition of a subject. In addition, an ultrasonic inspection apparatus is used for grasping a condition of a chest, an abdomen, etc, of the subject.

According to a related art, measurement of vital signs and ultrasonic diagnosis are simultaneously performed. For example, a related art system includes a patient monitor and an ultrasonic transducer connectable to the patient monitor (see, e.g., FIG. 1 of WO2009/138902A1). The system can simultaneously process both an ultrasonic image acquired by the ultrasonic transducer and physiological parameters (vital signs) of the subject.

With such a system, a medical personnel (such as a medical doctor) can refer to abdominal echo etc. together with the vital signs of the subject even in an operating room etc. without using a large-sized ultrasonic measuring apparatus. Thus, the medical personnel can refer to an ultrasonic image intermittently (in a spot) in order to grasp the condition inside the abdomen, for example, in the operating room etc.

When the medical personnel wants to check long-term changes in the vital signs, the medical personnel refers to a display screen of trend graphs indicating changes in measured values of the vital signs. However, according to the related art, the trend graphs and an image capture timing of the ultrasonic image are not provided in an associated manner. For example, the medical personnel cannot grasp the points on the trend graphs where the ultrasonic image has been captured, and cannot see the relationship between the vital signs and the ultrasonic image (such as an abdominal echo image) of the subject. Thus, the medical personnel cannot accurately grasp a change in the condition of the subject.

That is, it is difficult to grasp a relationship between the vital signs and the intermittently acquired ultrasonic images.

SUMMARY OF INVENTION

Illustrative aspects of the presently disclosed matter provide a patient monitor and a physiological information system that can grasp a relationship between a vital sign and intermittently captured ultrasonic images.

According to an aspect of the presently disclosed subject matter, a patient monitor patient monitor is configured to acquire vital signs based on vital sign signals of a subject and ultrasonic images based on ultrasonic waves transmitted toward the subject and received from the subject. The patient monitor includes a storage device configured to store measured data of the vital signs in association with measurement dates and times and to store the ultrasonic images in association with image capture tunings, and a controller configured to display a screen on a display section based on the measured data of the vital signs and the ultrasonic images stored in the storage device.

As described above, the storage device stores the measured data (measured values or measured waveforms) of the vital signs in association with the measurement dates and times. In addition, the storage device stores the ultrasonic images in association with the image capture timings. That is, both the measured data of the vital signs and the ultrasonic images are stored in association with the measurement dates and times (the image capture timings). Since the screen is generated based on the data associated in this manner, a user can grasp a relationship between the measured data of the vital signs and the ultrasonic images.

BRIEF DESCRIPTION OF DRAWINGS

FIG. 1 is a view illustrating an example of external configuration of a physiological information system 1 according to an embodiment of the presently disclosed subject matter.

FIG. 2 is a block diagram illustrating an internal configuration of the physiological information system 1.

FIG. 3 is a view illustrating an example of a screen displayed on a display section of the physiological information system.

FIG. 4 is a view illustrating another example of the screen displayed on the display section.

FIG. 5 is a view illustrating another example of the screen displayed on the display section.

FIG. 6 is a view illustrating another example of the screen displayed on the display section.

FIG. 7 is a view illustrating another example of the screen displayed on the display section.

FIG. 8 is a view illustrating another example of the screen displayed on the display section.

FIG. 9 is a view illustrating another example of the screen displayed on the display section.

FIG. 10 is a view illustrating another example of the screen displayed on the display section.

FIG. 11 is a view illustrating an example of a screen displayed on a display section according to another embodiment of the presently disclosed subject matter.

FIG. 12 is a view illustrating another example of the screen displayed on the display section of FIG. 11.

FIG. 13 is a view illustrating another example of the screen displayed on the display section of FIG. 11.

FIG. 14 is a view illustrating another example of the screen displayed on the display section of FIG. 11.

FIG. 15 is a view illustrating another example of the screen displayed on the display section of FIG. 11.

FIG. 16 is a view illustrating another example of the screen displayed on the display section of FIG. 11.

FIG. 17 is a view illustrating another example of the screen displayed on the display section of FIG. 11, FIG. 18 is a view illustrating a hardware configuration of a patient monitor according to an embodiment of the presently disclosed subject matter.

DESCRIPTION OF EMBODIMENTS

An embodiment of the presently disclosed subject matter will be described below with reference to the drawings. FIG. 1 is a conceptual diagram illustrating a configuration of external appearance of a physiological information system 1 according to the present embodiment. The physiological information system 1 has a patient monitor 10, and an ultrasonic measuring apparatus 20. The patient monitor 10 is configured to be connected to one or more sensors 30 (see FIG. 2).

The patient monitor 10 is configured to measure various vital signs based on vital sign signals sent from the various sensors 30 attached to a subject. The sensors 30 attached to the subject here serve as various sensors used for the measurement of the vital signs. For example, the sensors 30 include a cuff used for measurement of blood pressure, electrodes (such as disposable electrodes, clip electrodes, etc.) used for measurement of an electrocardiogram etc., an SpO2 probe, a mask used for measurement of respiration, etc. In addition, for example, the vital signs as targets to be measured include the blood pressure, body temperature, a respiration rate, arterial oxygen saturation, the electrocardiogram, and a pulse count. The patient monitor 10 is a concept including a bedside monitor, a wearable type medical telemeter, a defibrillator including a measurement function of an electrocardiogram etc., etc. That is, the patient monitor 10 can be interpreted to correspond to various medical apparatuses for measuring vital signs. In the following description, assume that the patient monitor 10 is a so-called bedside monitor.

The patient monitor 10 has connection ports (connector receptacles) to be connected to the various sensors 30. The ultrasonic measuring apparatus 20 is attachable to and detachable from the connection ports. For example, the ultrasonic measuring apparatus 20 and the patient monitor 10 may be connected to each other by a universal serial bus (USB) or may be connected to each other through a different type of connector. The ultrasonic measuring apparatus 20 is configured to acquire an ultrasonic image inside a body of a subject by placing a probe 21 in contact with (or brought close to) the body of the subject. The ultrasonic measuring apparatus 20 is configured to be light in weight and small in size enough to be held by a user (e.g., a medical doctor), and has a form like a typical ultrasonic diagnostic apparatus in which a cable is connected to a probe head.

The patient monitor 10 can display the ultrasonic image acquired by the ultrasonic measuring apparatus 20 on a display section 16.

The ultrasonic measuring apparatus 20 may have a configuration that can be connected to the patient monitor 10. That is, the ultrasonic measuring apparatus 20 is not limited to wired connection as illustrated in FIG. 1, but may be connected to the patient monitor 10 by wireless to transmit/receive data thereto/therefrom.

Next, a functional configuration of the physiological information system 1 will be described with reference to FIG. 2. FIG. 2 is a block diagram focused on the functional configuration of the physiological information system 1. As described above, each of the sensors 30 is a vital sign sensor connected (e.g., pasted) to the body of the subject.

The patient monitor 10 has an input interface 11, a communication section 12, an operating section 13, a controller 14, a speaker 15, the display section 16, and a storage device 17. Although not shown, the patient monitor 10 may further include a central processing unit (CPU) and/or an internal power supply. The patient monitor 10 may also include an internal clock (not shown) clocking a time instant.

The input interface 11 is the aforementioned connection ports and a peripheral circuit thereof. The input interface 11 supplies signals received from the sensors 30 and the ultrasonic measuring apparatus 20 to the controller 14. In addition, the input interface 11 transmits a signal from the patient monitor 10 to the sensors 30 or the ultrasonic measuring apparatus 20.

The communication section 12 transmits/receives data to/from another apparatus (e.g., a central monitor inside the same hospital). Any device may be used as the communication section 12 as long as the device satisfies a communication standard, for example, applied to a wireless local area network. (LAN) etc. The communication section 12 may perform communication processing using a wired cable.

The user (e.g., a medical doctor) performs an input to the patient monitor 10 through the operating section 13. For example, the operating section 13 serves as buttons, a knob, a rotary type selector, keys, etc. provided on a housing of the patient monitor 10. The input performed through the operating section 13 is supplied to the controller 14.

The speaker 15 outputs various notification sounds including an alarm. The speaker 15 performs notification in accordance with control of the controller 14.

The display section 16 includes a display provided on the housing of the patient monitor 10 and a peripheral circuit thereof. The display section 16 is configured to display measured waveforms or measured values of the various vital signs, ultrasonic images, etc. in accordance with control of the controller 14. In other words, the controller 14 displays, on the display section 16, a screen based on data (the ultrasonic images, measured data (the measured waveforms or the measured values) of the various vital signs, etc.) stored in the storage device 17. Display control performed by the controller 14 will be described later with reference to FIG. 3.

The operating section 13 and the display section 16 may be configured integrally with each other (may be configured as a touch panel). In the following description, assume that the operating section 13 and the display section 16 serve as the touch panel.

The storage device 17 stores various programs (including system software and software of various applications) or data (including the measured data including the measured values or the measured waveforms of the vital signs, dates and times when the measured data were measured, the ultrasonic images that will be described later, image capture timings of the ultrasonic images, etc.) to be used by the controller 14. The controller 14 properly reads the programs or the data from the storage device 17. In addition, the controller 14 writes data into the storage device 17 as necessary. The storage device 17 is a Secondary storage device provided inside the patient monitor 10, such as a hard disk provided inside the patient monitor 10. The storage device 17 is not limited to be built in the patient monitor 10, and may have a configuration that is attachable to and detachable from the patient monitor 10 (such as a universal serial bus (USB) memory etc. that is attachable to and detachable from the patient monitor 10).

The storage device 17 stores data (first data) in which the measured data (the measured values or the measured waveforms) of the vital signs acquired from the sensors 30 are made to correspond to the measurement dates and times, and stores data (second data) in which the ultrasonic images captured by the ultrasonic measuring apparatus 20 are made to correspond to the image capture timings of the ultrasonic images (the dates and times when the ultrasonic images were measured).

The controller 14 preforms action control of the patient monitor 10 (control of measurement through the sensors 30, reflection of various settings, import of an ultrasonic image, recording of measured values of vital signs, display control on the display section 16, etc.).

The controller 14 writes, into the storage device 17, the measured values of the various vital signs (blood pressure, a pulse count, body temperature, arterial oxygen saturation, a respiration rate, a respiration waveform, etc.) acquired through the sensors 30 in association with the measurement dates and times. The thing that the controller 14 continuously writes the measured values into the storage device 17 in association with the measurement dates and times is equivalent to the thing that the controller 14 stores the measured waveforms in association with the measurement dates and times. In addition, the controller 14 writes the ultrasonic images acquired by the ultrasonic measuring apparatus 20 into the storage device 17 in association with the image capture timings (the dates and times at which the images were taken or measured). The measurement dates and times are acquired with reference to data of the not-shown internal clock etc. The controller 14 displays, on the display section 16, a screen based on the data (the measured values of the vital signs and the ultrasonic images) stored in the storage device 17. Details of the display control will be described later with reference to FIG. 3 etc.

Next, the configuration of the ultrasonic measuring apparatus 20 will be described. The ultrasonic measuring apparatus 20 is an apparatus that is attachable to and detachable from the patient monitor 10, as illustrated in FIG. 1. The ultrasonic measuring apparatus 20 has the probe 21, a controller 22, and a storage device 23.

The ultrasonic measuring apparatus 20 may be an apparatus that receives electric power from the patient monitor 10 or may be configured to have an internal power supply.

The probe 21 makes contact with (or is close to) a body of a subject and transmits ultrasonic waves toward the body of the subject. The probe 21 also receives the ultrasonic waves (reflected waves) reflected from the body of the subject, and transmits the received ultrasonic waves to the controller 22.

The type of the probe 21 is not particularly limited. That is, the probe 21 may be of a convex type, a sector type, a linear type or any other type. In addition, operating interfaces (a knob, buttons, an operating wheel, etc.) may be provided on a housing of the probe 21. The user operates the operating interfaces to thereby change setting etc. of the probe 21.

The storage device 23 stores various software programs (including system software and software of various applications) or data (history values, setting values, etc. of ultrasonic images) to be used by the controller 22. The controller 22 properly reads the programs or the data from the storage device 23. In addition, the controller 22 properly writes data into the storage device 23. The storage device 23 is a secondary storage device provided in the ultrasonic measuring apparatus 20, such as a hard disk provided in the ultrasonic measuring apparatus 20. The storage device 23 is not limited to the case where the storage device 23 is built in the ultrasonic measuring apparatus 20, but may have a configuration that is attachable to and detachable from the ultrasonic measuring apparatus 20 (such as a USB (Universal Serial Bus) memory etc. that is attachable to and detachable from the ultrasonic measuring apparatus 20). The various software programs to be used by the ultrasonic measuring apparatus 20 may be stored in the patient monitor 10 (i.e. the storage device 17).

The controller 22 performs various settings of the probe 21 or imports or images a received signal acquired by the probe 21. Specifically, the controller 22 performs setting of beam forming of the probe 21, formation of an ultrasonic reception beam from received reflection, various signal processings (mode signal processing, CF signal processing, Doppler signal processing, etc.) on the ultrasonic reception beam, formation of an ultrasonic image by scanning processing, error detection of the probe 21, etc. In addition, the controller 22 transmits, to the patient monitor 10, the ultrasonic image formed from the received signal of the probe 21. The controller 22 may transfer the signal of the reflected wave acquired by the probe 21 directly to the patient monitor 10. In this case, the controller 14 performs processing for creating an ultrasonic image based on the signal of the reflected wave.

Assume here that the ultrasonic measuring apparatus 20 is not always used but an echo image etc. of an abdomen of a subject is acquired in a spot (intermittently). Screen control in the patient monitor 10 (the controller 14) when the ultrasonic image has been acquired intermittently will be described below.

FIG. 3 is a screen showing trend graphs (illustrating measured waveforms, typically long-time waveforms) of vital signs displayed on the display section 16. The controller 14 reads measured values of the various vital signs together with measurement dates and times from the storage device 17, and displays measured values v1 to v3 and measured waveforms w1 to w3 on the display section 16. On an upper portion of the screen, menus m1 to m5 are displayed, and the menu m1 about the trend graphs has been selected. In this example, the display section 16 displays trend graphs of a heart rate (HR), arterial oxygen saturation (SpO2) and a respiration rate (Resp) from 14:30 to 15:30 (w1 to w3 in FIG. 3). The display section 16 also displays operating buttons b1 to b5 on a lower portion of the screen.

The screen of FIG. 3 is merely an example. Kinds of the vital signs to be displayed may be optional. For example, trend graphs of vital signs about blood pressure, body temperature, and the like may be displayed.

The controller 14 displays image capture timings of ultrasonic images together with the trend graphs (w1 to w3, v1 to v3) of the vital signs on the screen. To display the image capture timings, the controller 14 determines display positions of the image capture timings from a relation between a timeline of the trend graphs and the measurement (imaging) dates and times of the ultrasonic images. In the example of FIG. 3, the controller 14 displays icons i1 to i4 indicating the image capture timings of the ultrasonic images. In the example of FIG. 3, the image capture timings are indicated by triangle marks on the timeline. Each of the triangle marks indicates a timing at which a corresponding one of the ultrasonic images has been captured. The icons indicating the image capture timings are merely examples, and may be other icons may alternatively be used. In addition, the image capture timings may be indicated by vertical lines (straight lines perpendicular to an advancing direction of the timeline) on the timeline. The controller 14 uses data read thus from the storage device 17 so as to display together the trend graphs of the vital signs and the image capture timings of the ultrasonic images on the display section 16.

By referring to the screen (FIG. 3), the user (mainly the medical doctor) can grasp not only long-term changes in the measured values of the various vital sings but also the image capture timings of the ultrasonic images. For example, the user can grasp whether or not the ultrasonic images are acquired at the timings at which the measured values of the vital signs decline.

By referring to the measured waveforms w1 to w3 of the vital signs, the user reviews a timing of an ultrasonic image the user desires to refer to. The user selects a desired image capture timing. For example, the user may press one of the icons of the image capture timings on the display section 16 formed as the touch panel. Assume here that the user has selected the icon i1.

Hereinafter, refer to FIG. 4. The controller 14 reads, from the storage device 17, an ultrasonic image corresponding to the image capture timing (the icon i1) that has been selected by the user. The controller 14 displays a window d1 about the read ultrasonic image on the screen.

The controller 14 may display the ultrasonic image corresponding to the selected image capture timing in a full screen mode.

In addition, the user may select the desired image capture timing (from the icons i1 to i4) not by an operation on the touch panel or by use of the buttons etc. provided on the housing of the patient monitor 10. For example, the user may operate the buttons to move the cursor and make selection so as to select the desired image capture timing (from the icons i1 to i4).

In addition, instead of displaying the ultrasonic image on the window d1 immediately after the image capture timing (the icon i1) has been selected, the controller 14 may display the ultrasonic image corresponding to the image capture timing (the icon i1) after the menu m5 (ultrasonic tab) has been selected. When the image capture timing (the icon i1) has been selected, the controller 14 may invert the color of the icon i1 to clearly show that the icon i1 has been selected.

In addition, the controller 14 may display the ultrasonic image and display together the measured values and/or the measured waveforms of the various vital signs acquired at the image capture timing of the ultrasonic image. Such a display example will be illustrated in FIG. 5. As illustrated in FIG. 5, the controller 14 displays a window d2 of the ultrasonic image, that includes not only the ultrasonic image corresponding to the selected image capture timing but also measured values (v4) of the various vital signs and an image capture timing (tm1). The measured values (v4) indicate measured values of the vital signs (e.g., measured values of the vital signs between 14:32:00 to 14:33:00) at the image capture timing (tm1). By referring to the display screen (FIG. 5), the user can grasp the measured values of the vital signs during the imaging together with image information of the abdominal echo image etc.

In the example of FIG. 3, the controller 14 creates a display screen displaying both a display area for the vital signs (a timeline of HR, SpO2 and Resp) and a display area for the image capture timings (a timeline of Ultrasound). According to another example, the controller 14 may display the icons of the image capture timings on the display area for the vital signs. An example of such a display screen will be illustrated in FIG. 6.

In the example of FIG. 6, the icons it to i4 indicating the image capture timings of the ultrasonic images are displayed on the measured waveform w1 of the heart rate HR. The display of FIG. 6 is merely an example. The icons indicating the image capture timings may be displayed on the measured waveforms of all the kinds of the vital signs.

Further, the controller 14 may change the display control to be performed in accordance with the operation pattern performed by the user. The controller 14 detects the pattern of operation performed by the user, in addition to the selected image capture timing. Specifically, the controller 14 detects the pattern of operation (tapping, double-tapping, pinch-in, pinch-out, flicking, etc.) performed on the image capture timing (or its vicinity).

The controller 14 determines a display mode of the ultrasonic image in accordance with the detected operation pattern. For example, when tapping operation has been performed on the icon of the image capture timing, the controller 14 displays a window indicating the target ultrasonic image, as illustrated in FIG. 4. On the other hand, when pinching-in operation has been performed on the icon of the image capture timing, the controller 14 displays the ultrasonic image as the display target in the full screen mode. The above correspondence between the operation patterns and the display controls is merely an example. Configuration may be made so that the user can define the correspondence. The display mode of the ultrasonic image may be changed in accordance with the operation pattern, so that the user can refer to the ultrasonic image in the desired display mode by less work.

Further, the controller 14 may perform display control so that the measured waveforms of the vital signs at the selected image capture timing do not overlap with the ultrasonic image. Such display control will be described with reference to FIGS. 7 and 8.

FIG. 7 is a display screen showing a state in which the image capture timing has not been selected yet. Assume here that the user selects the icon i3. A range in which the measured waveforms of the vital signs in a predetermined period of time including the image capture timing (the icon i3) are displayed is denoted as display area A1.

FIG. 8 is a view illustrating a screen when the icon i3 has been selected. As illustrated in FIG. 8, the controller 14 displays a window d3 of the ultrasonic image corresponding to the selected image capture timing (the icon i3). In addition, the controller 14 moves the display area A1 (the measured waveforms of the vital signs in the predetermined period of time including the selected image capture timing) in a direction toward an end portion of the screen (that is a left direction in the example of FIG. 8, a dashed line arrow direction) so as to prevent the display area A1 from overlapping with the window d3. Then, the controller 14 displays the ultrasonic image at a place other than the display area A1 (a place where the measured waveforms in the predetermined period of time are hidden on the screen, a range of from the center of the image to the vicinity of a right side of the image in the example of FIG. 8). That is, the controller 14 adjusts the display position (moves the display position) so that the ultrasonic image does not overlap with the measured waveforms of the vital signs during the imaging of the ultrasonic image. Accordingly, the controller 14 displays both the ultrasonic image and the measured waveforms of the vital signs on the screen. Thus, the user can check the ultrasonic image on a large window and can also grasp the states of the vital signs together during the imaging of the ultrasonic image.

In addition, when the user performs an operation of ending the display of the ultrasonic image (e.g., pushing down a "X" button or a close button of the window d3) in the display state of FIG. 8, it is preferable that the controller 14 performs display control to restore the measured waveforms of the vital signs to their original positions (i.e. the state of FIG. 7, the positions before the movement). By restoring the screen to the display in which the ultrasonic image has not been referred to yet, the user can grasp the condition of the subject smoothly.

The display control of FIG. 8 is merely an example. The display control of FIG. 8 may be made to move the measured waveforms of the vital signs toward a right end portion, an upper portion, a lower portion, an oblique lower portion, or an oblique upper portion. The display control of FIG. 8 may be made so that the measured waveforms of the vital signs can be displayed at the center and the ultrasonic image can be displayed at an end portion of the screen. The controller 14 may display a window in which the display area A1 and the window d3 have been combined (a mode of display in which the measured waveforms in the predetermined period of time do not overlap with the ultrasonic image) in a pop-up manner.

In addition, the controller 14 may create a screen including a plurality of ultrasonic images. Such an example will be described with reference to FIG. 9. The user selects another image capture timing in a state in which a window d4 of an ultrasonic image has been displayed. In the example of FIG. 9, the user selects another icon i1 in the state in which only the window d4 of the ultrasonic image (corresponding to the icon i2) has been displayed.

The controller 14 reads an ultrasonic image corresponding to the selected icon i1 and displays the read ultrasonic image on the screen. In the example of FIG. 9, the controller 14 displays both the window d4 of the ultrasonic image and a window d5 of the ultrasonic image. To allow display of windows of a plurality of ultrasonic images, it is preferable that the controller 14 performs display control so that the initially displayed window d4 does not overlap with the icons i1 to i4. In addition, the controller 14 may automatically adjust respective window sizes in accordance with the number of the windows to be displayed. When the plurality of ultrasonic images are displayed, the user can also grasp a change in abdominal echo images etc. on one screen.

Further, the controller 14 may display event information recorded in association with an image capture timing of each ultrasonic image. Such an example will be described with reference to FIG. 10.

The user inputs the event information associated with the ultrasonic image. For example, the event information includes a measured part of a body of a subject, information on a person who took the ultrasonic image (e.g., name of the person), information on the subject (e.g., age and/or gender of a subject), and an image capture date and time. The user may input the event information through the operating section 13 or the controller 14 may automatically calculate the event information. For example, the controller 14 may analyze the captured ultrasonic image to automatically calculate various parameters. The controller 14 writes the event information into the storage device 17.

Then, the user refers to the trend graphs of the vital signs as illustrated in FIG. 3, and selects an image capture timing as described above. The controller 14 reads an ultrasonic image corresponding to the selected image capture timing from the storage device 17. In addition, the controller 14 also reads the event information corresponding to the selected image capture timing from the storage device 17. The controller 14 displays together the read ultrasonic image and the read event information on a window d6 (FIG. 10). As illustrated in FIG. 10, the event information e1 (name, gender and age of a subject) are displayed together with the ultrasonic image.

By referring to the event information, the user can also grasp information that cannot be grasped only from the ultrasonic image. Thus, the user can grasp the situation of the subject in more detail.

In one or more of the display examples (FIG. 4, FIG. 5 and FIGS. 8 to 10), the user may change the size of the window on which the ultrasonic image is displayed, by drag processing. The controller 14 detects the drag processing to properly change the window size. In a similar manner or the same manner, the user may properly move the position of the window.

According to the patient monitor 10 described above, the storage device 17 stores the measured data (the measured values or the measured waveforms) of the vital signs in association with the measurement dates and times. In addition, the storage device 17 stores the ultrasonic images in association with the image capture timings. That is, the measured data of the vital signs and the ultrasonic images are stored together in association with the measurement dates and times (image capture timings). Thus, the measured data of the vital signs are associated with the ultrasonic images. By generating a screen based on the data associated in this manner, the user can grasp a relationship between the measured data of the vital signs and the ultrasonic images.

Further, when an image capture timing is selected in the screen (e.g., FIG. 3) displayed on the display section 16, the controller 14 displays an ultrasonic image corresponding to the image capture timing (FIG. 4). Thus, the user can visually grasp correspondence between the vital signs and the ultrasonic image. As described above, the controller 14 may display the ultrasonic image immediately after the image capture timing has been selected, or may display the ultrasonic image corresponding to the selected image capture timing after the menu (m5 in FIG. 3) about the ultrasound has been selected.

In addition, when measured values of the vital signs are displayed together with the ultrasonic image (FIG. 5), the user can more accurately grasp correspondence between the vital signs and the ultrasonic image.

When the ultrasonic image and the event information are displayed together (FIG. 10), the user can also grasp the various information (e.g., age) about the subject together with the ultrasonic image of the subject.

With reference to FIG. 7 and FIG. 8, the controller 14 may performed display control so that the ultrasonic image corresponding to the selected image capture timing does not overlap with the measured data (measured waveforms or measured values) of the vital signs at the image capture timing. Thus, the user can grasp the condition of the subject at the selected image capture timing in more detail. When the display region of the vital signs moves, particularly as illustrated in FIG. 8, the user can intuitively understand that the measured waveforms of the vital signs drawing user's attention (at the selected image capture timing) are displayed.

In addition, when a plurality of ultrasonic images are displayed (FIG. 9), the user can grasp a transition among the ultrasonic images (e.g., a transition of an abdomen condition of the subject).

Next, a physiological information system 1 according to another embodiment of the presently disclosed subject matter will be described below. A patient monitor 10 of the physiological information system 1 is configured to display an image list (e.g., a thumbnail screen) of a plurality of ultrasonic images so that (measured waveforms or measured values of) vital signs corresponding to an image capture timing of an ultrasonic image selected from the image list can be referred to.

The basic configuration of the physiological information system 1 and the patient monitor 10 thereof is similar to or the same as those of the foregoing embodiment. The patient monitor 10 displays a screen illustrated in FIG. 3 on a display section 16. When a user selects a menu m5 for performing display of ultrasonic images, a controller 14 reads, from a storage device 17, an ultrasonic image acquired at each image capture timing, and displays an image list of the ultrasonic images (or one ultrasonic image when only the ultrasonic image is present). For example, the controller 14 arranges the image list in which the read ultrasonic images have been converted into thumbnails in chronological order, and displays the arranged image list. The image list may be not the list of the thumbnails but may be a list of icons attached with file names, a list of the file names of the ultrasonic images, etc. As in the foregoing embodiment, when the user selects the menu m5 after having selected an image capture timing, the controller 14 may largely display only an ultrasonic image corresponding to the image capture timing, or may display only a thumbnail of the ultrasonic image in an emphasized manner in comparison with the other thumbnails (e.g., a frame line of the thumbnail may be displayed with a different color from frame lines of the other thumbnails). In the following description, assume that no image capture timing is selected preliminarily. FIG. 11 shows an example of such a screen in which ultrasonic images are displayed in thumbnail formats.

As illustrated in FIG. 11, a number of the taken ultrasonic images (u1 to u9) are displayed in the thumbnail formats in chronological order on the screen. The number of the ultrasonic images displayed within the screen may be fixed (e.g., up to 9). The controller 14 may display an icon of page feeding etc, to realize the page feeding.

The user selects (e.g., taps) a desired ultrasonic image (for which the user desires to refer to measured data of vital signs). The controller 14 reads, from the storage device 17, the measured data of the vital signs corresponding to an image capture timing of the ultrasonic image that has been selected from the image list. Specifically, the controller 14 reads, from the storage device 17, the measured data of the vital signs acquired in a predetermined period of time (e.g., in one minute) including the image capture timing of the selected ultrasonic image. The controller 14 creates a screen in which the read measured data of the vital signs are displayed. FIG. 12 is a view illustrating a screen example when the ultrasonic image u1 has been selected on the screen of FIG. 11.

As illustrated in FIG. 12, the controller 14 displays measured values or measured waveforms of the various vital signs at the image capture timing (14:04:26) of the selected ultrasonic image (u1) on a new window d7. The user can refer to the screen to thereby refer to the ultrasonic image in the thumbnail format and the measured values or the measured waveforms of the vital signs together.

The controller 14 may be configured to display the measured waveforms together with the measured values only when the user has increased the size of the window d7 by drag processing etc. The controller 14 properly determines whether the size of the window d7 has exceeded a predetermined size or not. When the size of the window d7 has exceeded the predetermined size, the controller 14 displays the measured waveforms together with the measured values. In addition, the controller 14 may be configured to display only the measured values when the size of the window d7 does not exceed the predetermined size, and to display the measured waveforms together with the measured values when the size of the window d7 has exceeded the predetermined size. That is, based on the size of the window displaying the measured data, the controller 14 changes a display mode of the window. By such display control, necessary minimum information can be referred to when the window size is small, and more detailed information can be referred to when the window size is large. The controller 14 may not display the new window but may display the measured values in the vicinity of the selected ultrasonic image (u1).

The controller 14 may change the display control to be performed in accordance with an operation pattern performed by the user. The controller 14 detects the operation pattern performed by the user, in addition to the selected image capture timing. Specifically, the controller 14 detects the operation pattern (tapping, double-tapping, pinch-in, pinch-out, flicking, etc.) performed at the image capture timing (or its vicinity).

The controller 14 determines the display control to be performed in accordance the detected operation pattern. For example, when the pinch-out operation (that is an operation of spreading fingertips out) is performed on the display of the ultrasonic image u1, the controller 14 displays an enlarged image of the selected ultrasonic image u1 (that means a size larger than display of a thumbnail but may be the same in aspect ratio as an actual file). On the other hand, when the double-tapping operation (that is an operation of tapping twice delicately with a fingertip) is performed on the display of the ultrasonic image u1, the controller 14 displays the measured values or the measured waveforms of the vital signs corresponding to the selected ultrasonic image u1 (FIG. 12). In addition, when the flicking operation (that is an operation of moving and flicking a finger) is performed on the display of the ultrasonic image u1, the controller 14 also displays measured values of the vital signs corresponding to the image capture timing of the selected ultrasonic image u1 together with the enlarged image of the ultrasonic image u1 (a window d8 in FIG. 13). That is, the controller 14 may display both or at least one of the enlarged image of the selected ultrasonic image u1 and the measured data (the measured waveforms or the measured values) of the vital signs. Correspondence between the above operations and the display controls is merely examples. Other correspondence than the aforementioned correspondence may be performed, or correspondence between operations and display controls may be defined by the user.

The user may set in advance an action that should be performed when an image is selected from the image list through the operating section 13. For example, when a thumbnail image has been selected in a state in which such setting has been performed, the controller 14 always displays an enlarged image corresponding to the selected thumbnail image.

The controller 14 may display a list 11 (a timing list) of image capture timings together when the enlarged image of the ultrasonic image u1 and the measured values of the vital signs are displayed, as illustrated in FIG. 14. In the example of FIG. 14, nine image capture timings are displayed. In the example, only time instants are displayed. However, both dates and times may be displayed. It is preferable that the controller 14 displays an image capture timing corresponding to an ultrasonic image that is being displayed, so that the image capture timing can distinguish from any other image capture timing. In the example of FIG. 14, the controller 14 draws an underline only on display of "14:04:26" because the ultrasonic image taken at "14:04:26" is displayed.

The user can select an image capture timing in the list 11 on the screen (e.g., touch a desired time instant) to thereby change the ultrasonic image u1 that is a display target. The controller 14 reads, from the storage device 17, an ultrasonic image corresponding to the image capture timing selected by the user, and displays an enlarged image of the read ultrasonic image. When the user has selected "15:15:46" (e.g., when the user has touched "15:15:46" on the screen) in the example of FIG. 14, the controller 14 reads an ultrasonic image taken at "15:15:46" from the storage device 17, and switches the display from the currently displayed ultrasonic image u1 taken at "14:04:26" to the read ultrasonic image u7 taken at "15:15:46".

The controller 14 may adjust a display position so that the selected ultrasonic image (thumbnail) and the measured values or the measured waveforms of the vital signs can be easily referred to together. Such an example will be described with reference to FIG. 15.

Assume that the user selects the ultrasonic image u5 on the screen of FIG. 11. The controller 14 acquires display coordinates of the ultrasonic image u5 (e.g., calculates the display coordinates of the ultrasonic image u5 based on coordinate information when the display screen is created), and recognizes that the ultrasonic image u5 is located substantially at the center of the screen. When determining that the ultrasonic image u5 is located substantially at the center, the controller 14 shifts the display position of the ultrasonic image u5 to an end portion of the screen, and displays a window d9 substantially at the center of the screen. The window d9 indicates measured values or measured waveforms of the vital signs. FIG. 15 is a view illustrating such a display example. As illustrated in FIG. 15, the ultrasonic image u5 moves in a direction toward a left end portion and the window d9 indicating the measured values or the measured waveforms of the vital signs is displayed at the center of the screen. That is, the controller 14 performs display control so that the ultrasonic image u5 does not overlap with the measured values or the measured waveforms of the vital signs. The screen of FIG. 15 is merely an example. The ultrasonic image u5 may be moved in a direction toward a right end portion or may be moved in another direction. That is, the controller 14 may control the display position so that the ultrasonic image u5 does not overlap with the window d9.

When the ultrasonic image u5 (the selected ultrasonic image) is moved thus, the user can grasp the ultrasonic image u5 and the measured values or the measured waveforms of the vital signs together. In other words, the user can grasp both an ultrasonic image and measured data (measured values or measured waveforms) of the vital signs acquired at a certain time point. Accordingly, the user can grasp a condition of a subject in more detail.

In addition, when one of the ultrasonic images u1 to u3 has been selected, it is preferable that the controller 14 displays a new window (an enlarged image of the ultrasonic image or information of the vital signs) on a lower portion of the screen. When one of the ultrasonic images u7 to u9 has been selected, it is preferable that the controller 14 displays a new window (an enlarged image of the ultrasonic image or information of the vital signs) on an upper portion of the screen. That is, the controller 14 determines a display position of the new window (a display position of the measured waveforms or the measured values of the vital signs) based on a display position of a thumbnail of the selected ultrasonic image. Thus, the user can refer to both the thumbnail and the new window without any feeling of wrongness.

The controller 14 may not display ultrasonic images other than the selected ultrasonic image (the ultrasonic image u1 in FIG. 12 or the ultrasonic image u5 in FIG. 15). FIG. 16 is a view illustrating an example in which the other ultrasonic images than the ultrasonic image u5 are not displayed on the screen of FIG. 15. Thus, the user can accurately grasp the ultrasonic image and the measured data (the measured waveforms or the measured values) of the vital signs acquired at the image capture timing drawing user's attention without being affected by the other images.

The controller 14 may display a plurality of windows displaying vital signs. Such a display example is illustrated in FIG. 17. For example, assume that, first, the user has selected the ultrasonic image u1. The controller 14 displays a window d10 of the vital signs so as not to overlap with the ultrasonic image u1, as illustrated in FIG. 17. When the user then has selected the ultrasonic image u9, the controller 14 displays a window d11 of the vital signs so as not to overlap with the ultrasonic images u9 and u1 and the window d10, as illustrated in FIG. 17. The user may perform drag processing to thereby properly move the windows d10 and d11.

According to the patient monitor 10 described, above, the controller 14 is configured to display the thumbnail screen of the ultrasonic images. When a thumbnail has been selected, the controller 14 displays measured data (measured waveforms or measured values) of the vital signs corresponding to an image capture timing of the selected ultrasonic image (e.g., FIG. 12). Thus, the user can gain access to information of the vital signs through the ultrasonic image and grasp a relationship between the both.

The controller 14 may control a display mode in accordance with the kind of operation performed by the user (FIG. 12 or 13). Thus, a target to be displayed can be changed dynamically in accordance with a difference between simple operations such as flicking and double-tapping so that the user can refer to desired information rapidly.

The controller 14 may display a plurality of windows in accordance with a user operation (FIG. 17). When the plurality of windows are displayed, the user can grasp while comparing information of the vital signs the user wants to refer to on one screen.

Event information may be displayed together also in the present embodiment. That is, the controller 14 may display the event information together with an enlarged image of the ultrasonic image or a window (e.g., d7) displaying information of the vital signs.

While the presently disclosed subject matter has been described with reference to certain embodiments thereof, the scope of the presently disclosed subject matter is not limited to the embodiments described above, and it will be understood by those skilled in the art that various changes and modifications may be made therein without departing from the scope as defined by the appended claims.

At least a portion of the aforementioned processing of the controller 14 may be implemented by a computer program operating inside the patient monitor 10. A hardware configuration example of the patient monitor 10 will be illustrated in FIG. 18. The patient monitor 10 has a CPU 101, a memory 102 (main storage device), a storage device 17, a display section 16, and a bus 103. The patient monitor 10 may be provided with a not-shown speaker, various electric circuits, etc. The elements of the patient monitor 10 are connected to one another through the bus 103.

The central processing unit (CPU) 101 expands data or a program necessary for execution of the aforementioned various processings of the controller 14 or the communication section 12 on the memory 102, and executes various commands included in the program. At least a portion of the various processings of the controller 14 may be implemented by a not-shown peripheral circuit etc.

Here, the program stored in any of various types of non-transitory computer readable media can be supplied to a computer. The non-transitory computer readable media include various types of tangible storage media. Examples of the non-transitory computer readable media include magnetic recording media (such as a flexible disk, a magnetic tape and a hard disk drive), magnetooptical recording media (such as a magnetooptical disk), a CD-read only memory (ROM), a CD-R, a CD-R/W, and semiconductor memories, such as a mask ROM, a programmable ROM (PROM), an erasable PROM (EPROM), a flash ROM, and a random access memory (RAM). In addition, the program may be supplied to the computer by any of the various types of transitory computer readable media. Examples of signals used for the transitory computer readable media include an electric signal, an optical signal and an electromagnetic wave. Each of the transitory computer readable media can supply the program to the computer through a wired communication line such as an electric wire or an optical fiber or through a wireless communication line.

The present application claims priority to Japanese Patent Application No. 2017-224419 filed on Nov. 22, 2017, the entire content of which is incorporated herein by reference.

The invention claimed is:

1. A patient monitor configured to acquire a vital sign based on a vital sign signal of a subject and ultrasonic images based on ultrasonic waves transmitted toward the subject and received from the subject, the patient monitor comprising:
a storage device configured to store measured data of the vital sign in association with measurement dates and times, and to store the ultrasonic images in association with image capture timings; and
a controller configured to:
display a screen on a display section based on data, including the measured data and the ultrasonic images, stored in the storage device, and
display a trend graph of the vital sign and a plurality of different image capture timings of the ultrasonic images based on the data read from the storage device, the
plurality of different image capture timings of the ultrasonic images being simultaneously displayed on the trend graph.

2. The patient monitor according to claim 1, wherein the controller is configured to read, from the storage device, and display one of the ultrasonic images corresponding to one of the image capture timings selected by a user.

3. The patient monitor according to claim 2, wherein the controller is configured to also display, when displaying the one of the ultrasonic images, a measured value of the vital sign acquired at the image capture timing of the one of the ultrasonic images.

4. The patient monitor according to claim 2, wherein the controller is configured to display a plurality of the ultrasonic images.

5. The patient monitor according to claim 2, wherein the controller is configured to display, together with the one of the ultrasonic images, event information associated with the one of the ultrasonic images.

6. The patient monitor according to claim 5, wherein the event information includes at least one of a measured part of a body of the subject, information about a person who took the one of the ultrasonic images, and an image capture date and time.

7. The patient monitor according to claim 2, wherein the controller is configured to perform a display control such that a measured waveform of the vital sign in a period of time including the selected one of the image capture timings do not overlap with the one of the ultrasonic images.

8. The patient monitor according to claim 7, wherein the controller is configured to move a display position of the measured waveform and to display the one of the ultrasonic images so as not to overlap with the moved display position of the measured waveform.

9. The patient monitor according to claim 8, wherein the controller is configured to restore, when an operation of ending the display of the ultrasonic image is performed, the measured waveform to an original position before the movement of the measured waveform.

10. The patient monitor according to claim 2, wherein the controller is configured to change a display mode of the ultrasonic image based on a pattern of a user operation.

11. The patient monitor according to claim 1, wherein the controller is configured to display an image list of one or more of the ultrasonic images read from the storage device, and to display the measured data of the vital sign corresponding to the image capture timing of one of the ultrasonic images selected from the image list.

12. The patient monitor according to claim 11, wherein the controller is configured to display an enlarged image of the one of the ultrasonic image selected from the image list.

13. The patient monitor according to claim 12, wherein the controller is configured to display a timing list of the image capture timings together with the enlarged image, the enlarged image corresponding to one of the image capture timings from the timing list.

14. The patient monitor according to claim 12, wherein the controller is configured to display both the enlarged image of the one of the ultrasonic images selected from the image list, and the measured data of the vital sign corresponding to the image capture timing of the one of the ultrasonic images.

15. The patient monitor according to claim 11, wherein the image list is a thumbnail list of the one or more of the ultrasonic images.

16. The patient monitor according to claim 15, wherein the controller is configured to display both a thumbnail of the selected one of the ultrasonic images and the measured data of the vital sign corresponding to the selected one of the ultrasonic images such that display positions of the thumbnail and the measured data are adjusted so as not to overlap each other.

17. The patient monitor according to claim 16, wherein the controller is configured to determine the display position of the measured data of the vital sign based on the display position of the thumbnail of the selected one of the ultrasonic images.

18. The patient monitor according to claim 11, wherein the controller is configured to change a display mode of a window displaying the measured data, based on a size of the window.

19. A physiological information system comprising:
a patient monitor configured to acquire a vital sign based on a vital sign signal of a subject; and
an ultrasonic measuring apparatus configured to acquire ultrasonic images based on ultrasonic waves transmitted toward the subject and reflected from the subject,
wherein the patient monitor comprises:
a storage device configured to store measured data of the vital signs in association with measurement dates and times, and to store the ultrasonic images in association with image capture timings; and
a controller configured to:
display a screen on a display section based on data, including the measured data and the ultrasonic images, stored in the storage device, and display a trend graph of the vital sign and a plurality of different image capture timings of the ultrasonic images based on the data read from the storage device, the plurality of different image capture timings of the ultrasonic images being simultaneously displayed on the trend graph.

* * * * *